(12) United States Patent
Yamada et al.

(10) Patent No.: US 7,462,453 B2
(45) Date of Patent: Dec. 9, 2008

(54) COMMON MARMOSET-DERIVED GLYCERALDEHYDE-3-PHOSPHATE DEHYDROGENASE GENE AND USE THEREOF

(75) Inventors: Toru Yamada, Nara (JP); Kenji Oeda, Kyoto (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/141,947

(22) Filed: Jun. 1, 2005

(65) Prior Publication Data
US 2005/0266474 A1 Dec. 1, 2005

(30) Foreign Application Priority Data
Jun. 1, 2004 (JP) ............................ 2004-162822
Mar. 4, 2005 (JP) ............................ 2005-060326

(51) Int. Cl.
*C12Q 1/68* (2006.01)
*C07H 21/04* (2006.01)
*C12N 5/06* (2006.01)
*C12N 9/02* (2006.01)

(52) U.S. Cl. .................... 435/6; 435/69.1; 435/189; 435/320.1; 435/363; 536/23.2; 536/23.1; 536/24.32

(58) Field of Classification Search ................. 435/194, 435/69.1
See application file for complete search history.

(56) References Cited

OTHER PUBLICATIONS

J. Biol. Chem 1988, vol. 263, pp. 15335-15341.*
Biosens & bioelectr. 2004, 9, 1537-1548.*
Hisham K. Hamadeh et al., "Gene Expression Analysis Reveals Chemical-Specific Profiles," *Toxicological Sciences* 67:219-231 (2002).
GenBank Accession AC146591 (p. 1 of printout).
GenBank Accession BC014085 (p. 1 of printout).
GenBank Accession NM_002046 (p. 1 of printout).
GenBank Accession AC146591 (p. 1 of printout), searched Sep. 15, 2002.
GenBank Accession BC014085 (p. 1 of printout), searched Mar. 25, 2004.
GenBank Accession NM_002046 (p. 1 of printout), searched Dec. 18, 2005.

* cited by examiner

*Primary Examiner*—Rebecca E. Prouty
*Assistant Examiner*—Md. Younus Meah
(74) *Attorney, Agent, or Firm*—Panitch Schwarze Belisario & Nadel LLP (57) ABSTRACT

The present invention provides a common marmoset-derived glyceraldehyde-3-phosphate dehydrogenase gene and use thereof.

22 Claims, 1 Drawing Sheet

COMMON MARMOSET-DERIVED GLYCERALDEHYDE-3-PHOSPHATE DEHYDROGENASE GENE AND USE THEREOF

BACKGROUND OF THE INVENTION

1. Field of the Invention

The present invention relates to a common marmoset-derived glyceraldehyde-3-phosphate dehydrogenase gene and use thereof.

2. Description of the Related Art

Due to species difference, it has been demanded to utilize experimental animals of species which are closer to human to assess medicinal properties, side effect or toxicity on human of a chemical substance to be used as an active ingredient in medicines.

Additionally, for detailed assessment of medicinal properties, side effect or toxicity of such chemical substance, it has been attempted to develop a method for analyzing effects of a chemical substance on gene expression in tissues from organisms exposed to the chemical substance (see, for example, Hamadeh, H. K. et al, Tox. Sci., 67, 219(2002)).

SUMMARY OF THE INVENTION

In such gene expression analysis, there may be variations in number of cells used for each sample, recovery of RNA, detection efficiency of expression product and the like, when different test samples, particularly, test samples derived from different individuals or different kinds of tissues are used. Accordingly, it becomes necessary to use "a polynucleotide as an internal standard which can be used to determine a standard of level of gene expression in a test sample for normalizing an amount of a transcript of a desired gene when a difference in levels of expression of the desired gene in two or more kinds of test samples is measured by measuring a difference in amounts of the transcript of the desired gene in said samples".

The present invention provides a common marmoset-derived glyceraldehyde-3-phosphate dehydrogenase gene which can be used as the internal standard in gene expression analysis using the miniature monkey called common marmoset (*Callithrix Jacchus*) that is one kind of New World Monkeys among small monkeys being paid an attention as an experimental animal.

That is, the present invention provides;

1. an isolated polynucleotide comprising a nucleotide sequence of a common marmoset-derived glyceraldehyde-3-phosphate dehydrogenase gene (hereinafter, sometimes referred to as the present gene);

2. a polynucleotide (hereinafter, sometimes referred to as the present polynucleotide) comprising a nucleotide sequence of a common marmoset-derived glyceraldehyde-3-phosphate dehydrogenase gene or a partial nucleotide sequence thereof, wherein said nucleotide sequence is selected from the group consisting of:

(1) the nucleotide sequence of SEQ ID NO: 1;
(2) a nucleotide sequence encoding an amino acid sequence which is substantially the same as the amino acid sequence of SEQ ID NO: 2;
(3) a nucleotide sequence having at least 95% nucleotide identity to the nucleotide sequence of SEQ ID NO: 1;
(4) a nucleotide sequence encoding an amino acid sequence having at least 95% amino acid identity to the amino acid sequence of SEQ ID NO: 2;
(5) a nucleotide sequence of DNA which has any of nucleotide sequences as defined in (1) to (4), and is complementary to a mature mRNA containing a region from a 5' cap to a poly(A) sequence; (6) a nucleotide sequence encoding an amino acid sequence of glyceraldehyde-3-phosphate dehydrogenase;
(7) a nucleotide sequence which is complementary to any of nucleotide sequences as defined in (1) to (6); (8) a partial nucleotide sequence comprising at least 15 consecutive nucleotides in any of nucleotide sequences as defined in (1) to (7);
(9) the nucleotide sequence represented by nucleotide numbers 622 to 1221 of the nucleotide sequence of SEQ ID NO: 1;
(10) a nucleotide sequence comprising 20 to 60 consecutive nucleotides which is selected from the nucleotide sequence represented by nucleotide numbers 622 to 1221 of the nucleotide sequence of SEQ ID NO: 1; and
(11) a nucleotide sequence which is complementary to any of nucleotide sequences as defined in (9) or (10);

3. a composition (hereinafter, sometimes referred to as the present composition) for detecting DNA or RNA, which comprises a polynucleotide of the above 2;

4. the composition according to the above 3, wherein said polynucleotide is immobilized on a carrier;

5. a method for measuring a difference in levels of expression of a desired gene in two or more kinds of test samples by measuring a difference in amounts of a transcript of the desired gene in said samples (hereinafter, sometimes referred to as the present measuring method 1), which comprises:

(1) a first step of measuring an amount of a transcript of a common marmoset-derived glyceraldehyde-3-phosphate dehydrogenase gene in two or more kinds of test samples using a polynucleotide of the above 2,
(2) a second step of measuring an amount of a transcript of a desired gene in said test samples using a polynucleotide for detecting the desired gene,
(3) a third step of normalizing the amount of the transcript of the desired gene measured in the second step in each test sample by using as an internal standard the amount of the transcript of the glyceraldehyde-3-phosphate dehydrogenase gene measured in the first step in said test sample, and
(4) a fourth step of comparing the normalized amounts of the transcript of the desired gene in two or more kinds of test samples, thereby measuring a difference in the relative amounts of the transcript of the desired gene in the test samples;

6. the method according to the above 5, wherein said test samples are samples derived from common marmoset;

7 a method for measuring a difference in levels of expression of a desired gene in two or more kinds of test samples by measuring a difference in amounts of a transcript of the desired gene in said samples (hereinafter, sometimes referred to as the present measuring method 2), which comprises:

(1) a first step of measuring an amount of a transcript of a common marmoset-derived glyceraldehyde-3-phosphate dehydrogenase gene in two or more kinds of test samples using a polynucleotide of the above 2,
(2) a second step of measuring an amount of a transcript of a desired gene in said test samples using a polynucleotide for detecting the desired gene,
(3) a third step of calculating an inverse of the ratio of the amount of the transcript of the glyceraldehyde-3-phosphate dehydrogenase gene measured in the first step in a test sample relative to the amount of the transcript of the glyceraldehyde-3-phosphate dehydrogenase gene measured in the first step in a test sample to be a standard, (4) a fourth step of normalizing the amounts of the transcript of the desired gene measured in the second step in the test samples by multiplying the amount of the transcript of the desired gene measured in the second step in each test sample with the inverse of the ratio calculated in the third step for said test sample, and (5) a fifth step of comparing the normalized amounts of the transcript of the desired gene in two or more kinds of test samples, thereby measuring a difference in the relative amounts of the transcript of the desired gene in the test samples;

8. the method according to the above 7, wherein said test samples are samples derived from common marmoset;

9. the method according to the above 7, wherein the method of measuring an amount of a transcript of a gene in the first step and/or the second step is performed by either a DNA array method or a quantitative reverse transcriptase-polymerase chain reaction method;

10. a method for measuring a difference in levels of expression of a desired gene in two or more kinds of test samples by measuring a difference in amounts of a transcript of the desired gene in said samples (hereinafter, sometimes referred to as the present measuring method 3), which comprises:

(1) a first step of measuring an amount of a transcript of a common marmoset-derived glyceraldehyde-3-phosphate dehydrogenase gene in two or more kinds of test samples using a polynucleotide of the above 2, (2) a second step of measuring an amount of a transcript of a desired gene in said test samples using a polynucleotide for detecting the desired gene, (3) a third step of normalizing the amount of the transcript of the desired gene measured in the second step in the test samples by calculating the ratio of the amount of the transcript of the desired gene measured in the second step in each test sample relative to the amount of the transcript of the glyceraldehyde-3-phosphate dehydrogenase gene measured in the first step in said test sample, and (4) a fourth step of comparing the normalized amounts of the transcript of the desired gene in two or more kinds of test samples, thereby measuring a difference in the relative amounts of the transcript of the desired gene in the test samples;

11. the method according to the above 10, wherein said test samples are samples derived from common marmoset; and 12. the method according to the above 10, wherein the method of measuring an amount of a transcript of a gene in the first step and/or the second step is performed by either a DNA array method or a quantitative reverse transcriptase-polymerase chain reaction method.

DETAILED DESCRIPTION OF THE PREFERRED EMBODIMENTS

The present invention will be explained in detail.

A small monkey utilized in the present invention is common marmoset (*Callithrix Jacchus*) which is one kind of New World Monkeys. The monkey is a miniature monkey belonging to Anthropoidea which is closer to human as compared with rodents, has a better breeding efficiency as compared with a big monkey, and is small and easy to handle.

The present gene is a common marmoset-derived glyceraldehyde-3-phosphate dehydrogenase gene. The gene has properties as a house-keeping gene. Specifically, expression of the gene is hardly modulated by various chemical treatments, presence or absence of diseases, physiological stimulations, and the like, and its transcript is expressed ubiquitously and constitutively in living tissues. By using a level of expression of the gene as an internal standard which can be a standard of level of expression of a gene in a test sample, it becomes possible to normalize an amount of a transcript of a desired gene. When gene expression analysis is performed on a particular species (e.g. marmoset species to which common marmoset belongs), it is particularly preferable to normalize an amount of a transcript of the gene using an amount of a transcript of a house-keeping gene derived from the species as a standard.

The present polynucleotide is a polynucleotide comprising a nucleotide sequence of a common marmoset-derived glyceraldehyde-3-phosphate dehydrogenase gene or a partial nucleotide sequence thereof, and said nucleotide sequence is any of the following nucleotide sequences:

(1) the nucleotide sequence of SEQ ID NO: 1;

(2) a nucleotide sequence encoding an amino acid sequence which is substantially the same as the amino acid sequence of SEQ ID NO: 2;

(3) a nucleotide sequence having at least 95% nucleotide identity to the nucleotide sequence of SEQ ID NO: 1;

(4) a nucleotide sequence encoding an amino acid sequence having at least 95% amino acid identity to the amino acid sequence of SEQ ID NO: 2;

(5) a nucleotide sequence of DNA which has any of nucleotide sequences as defined in (1) to (4), and is complementary to a mature mRNA containing a region from a 5' cap to a poly(A) sequence;

(6) a nucleotide sequence encoding an amino acid sequence of glyceraldehyde-3-phosphate dehydrogenase;

(7) a nucleotide sequence which is complementary to any of nucleotide sequences as defined in (1) to (6);

(8) a partial nucleotide sequence comprising at least 15 consecutive nucleotides in any of nucleotide sequences as defined in (1) to (7);

(9) the nucleotide sequence represented by nucleotide numbers 622 to 1221 of the nucleotide sequence of SEQ ID NO: 1;

(10) a nucleotide sequence comprising 20 to 60 consecutive nucleotides which is selected from the nucleotide sequence represented by nucleotide numbers 622 to 1221 of the nucleotide sequence of SEQ ID NO: 1; and (11) a nucleotide sequence which is complementary to any of nucleotide sequences as defined in (9) or (10).

As used herein, the "nucleotide sequence of DNA which has any of nucleotide sequences as defined in (1) to (4), and is complementary to a mature mRNA containing a region from a 5' cap to a poly(A) sequence" represented by the item number (5) is a nucleotide sequence of a polynucleotide generally called full length cDNA, which is a nucleotide sequence of DNA complementary to a mature mRNA containing a region from a 5' cap (including a 5' untranslated region, a protein coding region, and a 3' untranslated region) to a poly(A) sequence. The nucleotide sequence of the DNA retains properties as a house-keeping gene (hereinafter, sometimes referred to as the present properties). Specifically, a preferable example is a nucleotide sequence of a full length cDNA comprising the nucleotide sequence of SEQ ID NO: 1.

A representative example of the "nucleotide sequence encoding an amino acid sequence of glyceraldehyde-3-phosphate dehydrogenase" represented by an item number (6) includes a full length nucleotide sequence of a common marmoset-derived glyceraldehyde-3-phosphate dehydrogenase gene consisting of 1008 nucleotides, which is a nucleotide sequence encoding an amino acid sequence of a structural protein consisting of the amino acid sequence (335 amino acids) of SEQ ID NO: 2. An amino acid is encoded based on the information of a sequence of three nucleotides called codon, and it is known that there are plural kinds of codons which encode a particular amino acid. In the present invention, the "nucleotide sequence encoding an amino acid sequence of glyceraldehyde-3-phosphate dehydrogenase" refers collectively to all possible nucleotide sequences composed of different combination of codons as long as a change does not occur in the amino acid sequence to be encoded thereby and the nucleotide length thereof. Specifically, examples include (a) the nucleotide sequence of SEQ ID NO: 0.1, (b) a nucleotide sequence in which not less than 1 and not more than 20, preferably not less than 1 and not more than 10, further preferably not less than 1 and not more than 5 nucleotides in the nucleotide sequence of SEQ ID NO: 1 have been substituted so that a change does not occur in the amino acid sequence of SEQ ID NO: 2. Such the substitution of a nucleotide may be, for example, naturally occurring nucleotide substitution resulting from a difference in species, individuals or the like of the organism from which the nucleotide sequence is derived, or may be artificial nucleotide substitution (e.g. a nucleotide sequence in which nucleotide substitution has been introduced into DNA comprising a nucleotide sequence of a naturally-occurring glyceraldehyde-3-phosphate dehydrogenase gene by site-directed mutagenesis, a mutagenic treatment and the like described later).

The "partial nucleotide sequence" represented by the item number (8) is a nucleotide sequence contained in the present gene or a primer or a probe which is used for obtaining or detecting the present gene. The "partial nucleotide sequence" comprises at least 15 consecutive nucleotides in any of nucleotide sequences described in item numbers (1) to (7) and is shorter in a length than any of nucleotide sequences described in item numbers (1) to (9). Specifically, examples include the nucleotide sequence of SEQ ID NO: 3, the nucleotide sequence of SEQ ID NO: 4, any of nucleotide sequences described in item numbers (9) to (11) and the like.

Regarding definition of the "substantially the same amino acid sequence" represented by the item number (2), generally, it is the well known fact that, when an amino acid sequence of a protein having physiological activity is slightly changed, for example, even when there is a change of deletion, substitution or addition of one or plural amino acids in the amino acid sequence, physiological activity of the protein is maintained in some cases. As used herein, the substantially the same amino acid sequence means that, as far as properties (i.e. the present properties) as a house-keeping gene which is substantially equivalent to that of a particular amino acid sequence (i.e. the amino acid sequence of SEQ ID NO: 2) is retained, a mutated protein in which one or plural amino acids in the amino acid sequence have been deleted, substituted or added is also included in the scope of the present invention. The number of amino acids which have been altered in the foregoing is at least one residue, specifically, 1 or a few (herein, "a few" is around 2 to about 10) or more. Such the number of alterations may be within the range in which the present properties of the protein is maintained. More specifically, this is alteration in which not less than 1 and not more than 20, preferably not less than 1 and not more than 10, further preferably not less than 1 and not more than 5 amino acids in the amino acid sequence encoded by the nucleotide sequence of SEQ ID NO: 1 have been deleted, substituted or added. Such the mutation may be, for example, naturally occurring mutation resulting from processing which the protein undergoes in the cell, or a difference in species, individuals, organs, tissues or the like of the organism from which the protein is derived, or may be an artificial amino acid mutation (e.g. mutation of an amino acid located in an amino acid sequence of a protein produced by introducing a mutation into DNA comprising a nucleotide sequence encoding an amino acid sequence of a native protein to express it, by a site-directed mutagenesis, a mutagenic treatment and the like. Specific examples of a mutant protein comprising "a nucleotide sequence encoding an amino acid sequence which is substantially the same as the amino acid sequence of SEQ ID NO: 2" include a naturally occurring allelic variant of a glyceraldehyde-3-phosphate dehydrogenase comprising the amino acid sequence of SEQ ID NO: 2, wherein said variant is encoded by a polynucleotide which hybridizes to a complement of a polynucleotide comprising the nucleotide sequence of SEQ ID NO: 1 under a stringent condition described later.

Such the mutant protein having deletion, substitution or addition of amino acids may contain a conservatively substituted amino acid sequence. This means that a particular amino acid residue is substituted by a residue having physicochemical similarity which is similar in hydrophobicity, charge, pK or stereo-structural feature. Non-limited examples of such the conservative substitution include substitution between aliphatic chain-containing amino acid residues, and substitution between polar residues such as substitution among a group of (1) glycine and alanine; (2) valine, isoleucine and leucine; (3) aspartic acid, glutamic acid, asparagine and glutamine; (4) serine and threonine; (5) lysine and arginine; (6) phenylalanine and tyrosine.

Mutant proteins having deletion, substitution or addition of amino acids can be obtained, for example, by performing site-directed mutagenesis [e.g. a method (Gapped Duplex method, Nucleic Acids Res., 12, 9441-9456, 1984) utilizing amber mutation described in Nelson and McClelland, Methods Enzymol, 216; 279, 1992, a method by PCR utilizing primers for introducing a mutation and the like] on a gene having a nucleotide sequence encoding an amino acid sequence thereof according to the known technique.

Site-directed mutagenesis can be performed using a synthetic primer containing a mutation to be introduced. That is, using the aforementioned synthetic oligonucleotide and a primer having a nucleotide sequence which is complementary to the nucleotide sequence thereof as primers, an amplification reaction is performed using a plasmid containing a common marmoset-derived wild-type glyceraldehyde-3-phosphate dehydrogenase gene as a template. Then, by treatment with Dpn I which is a methylation-sensitive restriction enzyme, only a newly generated DNA having the mutation is left. *Escherichia coli* XLI-Blue strain is transformed using the reaction solution, and spread on an ampicillin-containing LB agar plate. The plate is incubated at 37° C. overnight, and a plasmid is isolated from the grown colonies. Thereby, a plasmid containing a mutated DNA can be obtained. As a kit based on the aforementioned method, for example, Quick-Change Site-Directed Mutagenesis Kit (manufactured by Stratagene) may be utilized. Introduction of intended mutation can be confirmed by determining its nucleotide sequence.

In addition to the aforementioned site-directed mutagenesis, further examples of a method of performing deletion, substitution or addition of amino acids include a method of treating a gene with a mutagen, and a method of cleaving a gene with a restriction enzyme, followed by removing, adding or substituting a selected gene fragment, and further followed by ligating it.

As used herein, the "wild-type glyceraldehyde-3-phosphate dehydrogenase gene" means a glyceraldehyde-3-phosphate dehydrogenase gene comprising a nucleotide sequence encoding the amino acid sequence most frequently occurring in nature, in amino acid sequences of the protein derived from the organism of the same species. Specifically, examples include a glyceraldehyde-3-phosphate dehydrogenase gene comprising the nucleotide sequence of SEQ ID NO: 1.

The "amino-acid identity" and the "nucleotide identity" in the present invention refer to identity and homology of sequences between two proteins or two DNAs or RNAs. The "identity" is determined by comparing two sequences which are aligned in the optimal state over an entire region of sequences to be compared. Herein, proteins or DNAs or RNAs to be compared may have addition or deletion (e.g. gap) of residues in the optimal alignment of two sequences. Such the identity can be calculated through a step of producing alignment utilizing ClustalW algorithm (Nucleic Acid Res., 22(22):4673-4680(1994)) using Vector NTI. The identity is measured using a sequence analysis software, specifically, Vector NTI, GENETYX-MAC, analysis tools provided by public databases and the like. The public databases are generally available, for example, at the Web site (http://www.ddbj.nig.ac.jp) of the DNA Data Bank of Japan (the international databank operated within the Center for Information Biology and DNA Data Bank of Japan).

The "amino acid identity" in the present invention may be calculated on the basis of an amino acid sequence and, for example, about 95% or more is preferable. The "nucleotide identity" may be calculated on the basis of a nucleotide sequence and, for example, about 95% or more is preferable.

The present gene or the present polynucleotide may be obtained by hybridization method or PCR method. It may be obtained using any method as far as these can be obtained.

For example, they can be obtained from a tissue of marmoset such as common marmoset, or a cultured cell derived from the animal according to genetic engineering methods described in Sambrook, J. et al., Molecular Cloning: A laboratory Manual 3rd edition, Cold Spring Harbor Laboratory Press (2001).

First, total RNA derived from a tissue of marmoset such as common marmoset or a cultured cell derived from the animal is prepared.

Specifically, for example, a tissue such as liver of common marmoset is homogenized in a solution containing a protein denaturing agent such as guanidine hydrochloride and guanidine thiocyanate, and phenol or chloroform is added to the homogenate to denature the proteins. After the denatured proteins are removed by centrifugation, total RNA is extracted from the recovered supernatant fraction by a method such as guanidine hydrochloride/phenol method, SDS-phenol method, and guanidine thiocyanate/CsCl method. Examples of a commercially available kit based on these methods include Trizol reagent (Invitrogen Corp.) and Isogen (manufactured by Nippon Gene CO., Ltd.).

Then, an oligo dT primer is annealed to a polyA sequence of the RNA using the resulting total RNA as a template, and a single-stranded cDNA is synthesized with a reverse transcriptase. Further, using the single-stranded cDNA as a template together with a primer which is an RNA fragment obtained by inserting a nick and a gap into the RNA strand using *Escherichia coli* RnaseH, a double-stranded cDNA maybe synthesized using *Escherichia coli* DNA polymerase I. The resulting cDNA is purified and recovered by a conventional method such as phenol chloroform extraction, and ethanol precipitation. Examples of a commercially available kit based on these methods include cDNA synthesis system plus (manufactured by Amersham Biosciences Corp.) and SuperScript Choice system (manufactured by Invitrogen Corp.).

Then, by ligating the resulting double-stranded cDNA using, for example, a vector such as a plasmid pUC118 or a phageλ gt10, and a ligase, a cDNA library can be prepared.

Alternatively, a genomic DNA is prepared from a tissue sample of common marmoset or a cultured cell derived from the animal according to a conventional method described, for example, in Sambrook, J. et al., Molecular Cloning: A laboratory Manual 3rd edition, Cold Spring Harbor Laboratory Press (2001), or Masami Muramatu, "Laboratory Manual Genetic Engineering" (Maruzen 1998).

For example, when a sample is liver, an extraction buffer [10 mM Tris-HCl (pH8.0), 0.1 mM EDTA (pHB8.0), 20 µg/ml, 0.5% SDS] is added at a 10-fold amount (v/w) a tissue weight, the sample is homogenized and, further, ProteinaseK is added to the final concentration of 100 µl/ml, followed by mixing. This mixture is incubated at 50° C. for 3 hours, and phenol/chloroform is added to denature proteins. After the denatured proteins are removed by centrifugation, ethanol is added to the recovered supernatant fraction, and a genomic DNA is precipitated and recovered. In addition, when a sample is peripheral blood, the sample can be treated using DNA-Extraction kit (manufactured by Stratagene) to obtain a genomic DNA. By ligating the resulting genomic DNA using a vector such as λgt10 and a ligase, a genomic DNA library can be obtained.

From the aforementioned single-stranded or double-stranded cDNA itself or cDNA library or genomic DNA library, the present gene or the present polynucleotide can be obtained by a PCR using, as a primer, an oligonucleotide having a partial nucleotide sequence of the nucleotide sequence of SEQ ID NO: 1 or the nucleotide sequence which is complementary to the partial nucleotide sequence, or alternatively, from the cDNA library genomic library, the present gene or the present polynucleotide can be obtained by a hybridization method using, as a probe, DNA having the nucleotide sequence of SEQ ID NO: 1 or a partial nucleotide sequence of the nucleotide sequence.

Examples of the primer used in PCR include an olegonucleotide of about 15 to about 50 nucleotides in length, which has a nucleotide sequence starting from a translation initiating point located at 5' end of the nucleotide sequence of SEQ ID NO: 1, and an oligonucleotide having a nucleotide sequence which is complementary to a nucleotide sequence starting from a translation terminating point located at 3' end of the nucleotide sequence of SEQ ID NO: 1. Specifically, examples of a forward primer include an oligonucleotide comprising the nucleotide sequence of SEQ ID NO: 3. Examples of a reverse primer include an oligonucleotide comprising the nucleotide sequence of SEQ ID NO: 4. As condition of PCR, for example, using a reaction solution having a composition containing 5 µl of Ex-Taq polymerase 10-fold concentrated buffer (manufactured by Takara Bio Inc.), 5 µl of a 2.5 mM dNTP mixed solution (containing each 2.5 mM of dATP, dGPT, dCTP and dTTP) (final concentration of each of dATP, dGTP, dCTP and dTTP is 0.25 mM), each 0.5 to 2.5 µl of 10 µM primers (final concentration is 0.1 to 0.5 µM), 0.1 to 0.5 µg of a template cDNA, and 1.25 units of Ex-Taq polymerase (manufactured by Takara Bio Inc.) in 50 µl of the reaction solution, an amplification cycle of 3 steps under the following condition is repeated. First, as a denaturation step, for example, incubation is performed at about 90°

C. to about 96° C., preferably about 94° C. to about 95° C. for 1 minute to 15 minutes, preferably 1 minute to 2 minutes. Then, as a step of annealing primers, for example, incubation is performed at about 30° C. to about 70° C., preferably about 40° C. to about 60° C. for about 3 seconds to about 3 minutes, preferably about 5 seconds to about 2 minutes. Further, as a step of elongation with a DNA polymerase, for example, incubation is performed at about 70° C. to about 75° C., preferably about 72° C. to about 73° C. for about 15 seconds to about 5 minutes, preferably about 30 seconds to about 4 minutes. The amplification cycle consisting of the three steps is performed about 20 times to about 50 times, preferably about 25 times to about 40 times. DNA amplified by such the PCR is purified by subjecting to low melting point agarose electrophoresis, if necessary, and recovered by ethanol precipitation, or it can be purified and recovered, for example, using a commercially available column for purifying DNA such as QIAquick PCR Purification Kit (manufactured by Qiagen). As a solvent for dissolving DNA upon recovery, a suitable solution such as water, physiological saline, 1 to 100 mM Tris hydrochloric acid, and TE buffer [10 mMTris, hydrochloric acid, 1 mM EDTA, pH 7.4 to 8.0] can be used.

Examples of a probe used in a hybridization method include a polynucleotide comprising the nucleotide sequence of SEQ ID NO: 1, and a polynucleotide having a partial nucleotide sequence of the polynucleotide. Examples of condition of hybridization include a stringent condition in which incubation is performed at 65° C. in the presence of 6×SSC (0.9M sodium chloride, 0.09M sodium citrate), 5× Denhart solution (0.1% (w/v) Ficoll400, 0.1% (w/v) polyvinylpyrrolidone, 0.1% (w/v) BSA, 0.5% (w/v) SDS and 100 μg/ml denatured salmon sperm DNA, then, incubation is performed two times at room temperature for 15 minutes in the presence of 1×SSC (0.15M sodium chloride, 0.015M sodium citrate) and 0.5% (w/v) SDS and, further, incubation is performed at 68° C. for 30 minutes in the presence of 0.1×SSC (0.015M sodium chloride, 0.0015M citrate) and 0.5% (w/v) SDS. Additional examples include a stringent condition in which incubation is performed at 65° C. in the presence of 5×SSC, 50 mM HEPES pH 7.0, 10× Denhart solution and a 20 μg/ml denatured salmon sperm DNA and, then, incubation is performed at room temperature for 30 minutes in 2×SSC and, further, incubation is performed two times at 65° C. for 40 minutes in 0.1×SSC. The present gene or the present polynucleotide can be also prepared by performing chemical synthesis of a nucleic acid based on the nucleotide sequence of SEQ ID NO: 1 according to a conventional method such as a phosphite-triester method (Hunkapiller, M. et al, Nature, 310, 105, 1984).

The obtained present gene or present polynucleotide can be cloned into a vector according to genetic engineering methods described, for example in Sambrook, J. et al., Molecular Cloning: A laboratory Manual 3rd edition, Cold Spring Harbor Laboratory Press (2001)

Specifically, cloning can be performed using a commercially available plasmid vector such as TL cloning kit (Invitrogen Corp.) and pBluescriptII (Stratagene). A nucleotide sequence of the resulting present gene or present polynucleotide can be confirmed according to a Maxam Gilbert method (described, for example, in Maxam, A. M. & W. Gilbert, Proc. Natl. Acad. Sci., USA, 74, 560, 1977) of a Sanger method (described, for example in Sanger, F. & A. R. Coulson, J. Mol. Biol., 94, 441, 1975, Sanger, F. & Nicklen & A. R. Coulson, Proc. Natl. Acad. Sci., USA, 74, 5463, 1977). When an automatic DNA sequencer such as Model 377 manufactured by ABI is used, a corresponding DNA sequencing kit such as Big Dye Terminator Cycle Sequencing Ready Reaction Kit manufactured by ABI can be used.

Among the present polynucleotide, a polynucleotide (hereinafter, referred to as the present full length cDNA in some cases) comprising a nucleotide sequence which is "a nucleotide sequence of DNA which has any of nucleotide sequences as defined in (1) to (4), and is complementary to a mature mRNA containing a region from a 5' cap to a poly(A) sequence" represented by the item number (5) (i.e. a nucleotide sequence of a polynucleotide called full length DNA), and is a nucleotide sequence of DNA which is complementary to a mature mRNA containing a region from a 5' cap (including a 5' untranslated region, a protein coding region, and a 3' untranslated region) to a poly(A) sequence, in which a nucleotide sequence of the DNA is such that properties (i.e. the present properties) as a house-keeping gene is retained, may be obtained, for example, using the following method.

For example, it is obtained from a tissue of common marmoset according to a method of obtaining a full length cDNA described in Japanese examined patent publication No. Hei 9-24818 or Japanese examined patent publication No. Hei 10-12729.

Specifically, for example, a total DNA is extracted from liver of common marmoset based on the aforementioned method. Then, a molecule which is to be a tag for a diol structure specific for a 5' cap site (7MeGpppN) is chemically bound thereto using the resulting total RNA as a template, an oligo dT primer is annealed to a polyA sequence of the RNA using this RNA as a template, a single-stranded cDNA is synthesized with a reverse transcriptase, and only a full length cDNA is separated utilizing the function of the tag molecule. The resulting full length cDNA is ligated using a vector such as a plasmid pUC118 or a phage λgt10, and a ligase to prepare a cDNA library.

From the obtained full length cDNA library, the polynucleotide can be obtained by a hybridization method using, as a probe, DNA having the nucleotide sequence of SEQ ID No: 1 or a partial nucleotide sequence of the nucleotide sequence. Examples of a probe used in a hybridization method include a polynucleotide comprising the nucleotide sequence of SEQ ID No: 1, and a polynucleotide comprising a partial nucleotide sequence of the polynucleotide. Examples of condition of hybridization include the aforementioned condition.

Alternatively, the present full length cDNA may be also obtained based on a nucleotide sequence of the present gene using RACE method utilizing PCR described in Frohman, M. A. et al., Proc. Natl. Acad. Sci., USA., 85, 8998 (1988), Junichiro Inoue, Kentaro Senba, "Separate Volume Experimental Medicine: cDNA Cloning" (Yodosha, 1996).

Specifically, for example, in order to obtain a 5'-terminal cDNA fragment, single-stranded cDNA is synthesized from a tissue of common marmoset by the aforementioned method. An oligonucleotide having a unique nucleotide sequence is added to the 3' terminus of the first strand of the synthesized cDNA (antisense-strand cDNA) using terminal deoxynucleotidyl transferase. As a unique nucleotide sequence, any nucleotide sequence may be used as far as it can hardly form unnecessary secondary structure, and it has no similarity with a nucleotide sequence of the present gene, and has high specificity. Examples include polydA consisting of 18 nucleotides to 24 nucleotides. PCR is performed using, as a template, cDNA (sense-strand cDNA) to which the oligonucleotide has been added at the 5' terminus thereof. Among primers used in the PCR, examples of a forward primer include an oligonucleotide having a nucleotide sequence which is complementary to the aforementioned oligonucleotide added to the cDNA using terminal deoxynuleotidyl transferase. Examples of a reverse primer include an oligonucleotide of about 15 to about 50 nucleotides in length, which has a nucleotide sequence complementary to a nucleotide sequence apart downstream from a translation initiating point located at the 5' end of the nucleotide sequence of SEQ ID No: 1 by a few tens to a few thousands nucleotides. Specifically, examples of the forward primer include polydT having 18 nucleotides to 24 nucleotides. Examples of the reverse primer include an oligonucleotide comprising the nucleotide sequence of SEQ ID No: 4. Examples of condition of the PCR include the aforementioned condition. In order to obtain a 3'-terminal cDNA fragment, total RNA is extracted from a tissue of common marmoset, an oligo dT primer with an adaptor sequence added to the 5' terminus thereof is annealed to a polyA sequence of RNA, and a single-stranded cDNA is synthesized with reverse transcriptase. As a nucleotide sequence of an oligo dT primer with an adaptor sequence added thereto, any nucleotide sequence may be used as far as it can hardly form unnecessary secondary structure, and it has no similarity with a nucleotide sequence of the present gene, and has high specificity. Examples include an oligonucleotide comprising the nucleotide sequence of SEQ ID NO: 5. PCR is performed using, as a template, a first strand of the synthesized cDNA (antisense-strand cDNA). Among primers used in the PCR, examples of a forward primer include an oligonucleotide of about 15 nucleotides to about 50 nucleotides in length, which has a nucleotide sequence apart upstream from a translation terminating point located at 3' end of the nucleotide sequence of SEQ ID No: 1 by a few tens to a few thousands nucleotides. Examples of a reverse primer include an oligonucleotide having a nucleotide sequence which is complementary to the adaptor sequence. Specifically, examples of the forward primer include an oligonucleotide comprising the nucleotide sequence of SEQ ID No: 3. In addition, examples of the reverse primer include an oligonucleotide comprising the nucleotide sequence of SEQ ID NO: 6. Examples of condition of the PCR include the aforementioned condition. After the thus obtained 5'-end cDNA fragment, 3'-end cDNA fragment and the present gene are cut with suitable restriction enzymes, the resulting fragments are ligated with a ligase, thereby, the present full length cDNA can be obtained.

The obtained present full length cDNA can be cloned into a vector according to genetic engineering methods described, for example, in Sambrook, J. et al., Molecular Cloning: A laboratory Manual 3rd edition, Cold Spring Harbor Laboratory Press (2001). Specifically, cloning can be performed using a commercially available plasmid vector such as TA cloning kit (Invitrogen Corp.) and pBluescriptII (Stratagene). A nucleotide sequence of the resulting present full length cDNA can be confirmed according to the aforementioned Maxam Gilbert method or Sanger method.

The present polynucleotide used for detecting DNA or RNA will be explained (hereinafter, referred to as the present polynucleotide for detecting DNA in some cases).

The present polynucleotide for detecting DNA is a polynucleotide comprising any of the following nucleotide sequences:

(9) the nucleotide sequence represented by nucleotide numbers 622 to 1221 of the nucleotide sequence of SEQ ID NO: 1;

(10) a nucleotide sequence comprising 20 to 60 consecutive nucleotides which is selected from the nucleotide sequence represented by nucleotide numbers 622 to 1221 of the nucleotide sequence of SEQ ID NO: 1; and (11) a nucleotide sequence which is complementary to any of nucleotide sequences as defined in (9) or (10).

Examples of a nucleotide sequence represented by the item number (10) include (10a) a nucleotide sequence comprising consecutive optional 60 nucleotides, selected from the nucleotide sequence represented by nucleotide numbers 622 to 1221 of the nucleotide sequence of SEQ ID NO: 1. (10b) a nucleotide sequence comprising consecutive optional 50 nucleotides, selected from the nucleotide sequence represented by nucleotide numbers 622 to 1221 of the nucleotide sequence of SEQ ID NO: 1, (10c) a nucleotide sequence comprising consecutive optional 35 nucleotides, selected from the nucleotide sequence represented by nucleotide numbers 622 to 1221 of the nucleotide sequence of SEQ ID NO: 1, (10d) a nucleotide sequence comprising consecutive optional 30 nucleotides, selected from the nucleotide sequence represented by nucleotide numbers 622 to 1221 of the nucleotide sequence of SEQ ID NO: 1, and (10e) a nucleotide sequence comprising consecutive optional 20 nucleotides, selected from the nucleotide sequence represented by nucleotide numbers 622 to 1221 of the nucleotide sequence of SEQ ID NO: 1.

The present polynucleotide for detecting DNA having any of characteristics of the item numbers (9) to (11) can be selected according to similarity with nature of one or more polynucleotides separately used for detecting a desired gene to be analyzed. For example, when a DNA array for detecting DNA or RNA is employed using a long cDNA as described later, it is preferable to use a polynucleotide comprising the nucleotide sequence represented by nucleotide numbers 622 to 1221 of SEQ ID NO: 1 shown in the item number (9). In addition, when DNA or RNA is detected by a method such as a DNA array and RT-PCR using a short polynucleotide, it is preferable to use any of polynucleotides comprising a nucleotide sequence represented by the item number (10) or (11). Specifically, examples of a nucleotide sequence represented by the item number (10) include a consecutive nucleotide sequence of 60 nucleotides in length, which begins at any nucleotide of nucleotide number 805 to 806, 853 to 858, or 906 to 943 of the nucleotide sequence of SEQ ID No: 1, and terminates at any nucleotide of nucleotide number 864 to 865, 912 to 917, or 965 to 1002 of the nucleotide sequence of SEQ ID NO: 1, respectively. In addition, examples include a consecutive nucleotide sequence of 50 nucleotides in length, which begins at any nucleotide of nucleotide number 613, 643, 649 to 650, 653 to 656, 679, 750 to 756, 807 to 847, 902 to 927, 1005, 1039, 1057 to 1058, 1070 to 1086, or 1140 to 1160 of the nucleotide sequence of SEQ ID No: 1, and terminates at any nucleotide of nucleotide number 662, 692, 698 to 699, 702 to 705, 728, 799 to 805, 856 to 896, 951 to 976, 1054, 1088, 1106 to 1107, 1119 to 1135 or 1189 to 1209 of the polynucleotide sequence of SEQ ID No: 1, respectively. In addition, examples include a consecutive nucleotide sequence of 35 nucleotides in length, which begins at any nucleotide of nucleotide number 649 to 671, 808 to 811, 816 to 862, 902 to 942, 967 to 980, 1018, 1028 to 1042, 1070 to 1101, or 1150 to 1175 of the nucleotide sequence of SEQ ID No: 1, and terminates at any nucleotide of nucleotide number 683 to 705, 842 to 845, 850 to 896, 936 to 976, 1001 to 1014, 1052, 1062 to 1076, 1104 to 1135, or 1184 to 1209 of the nucleotide sequence of SEQ ID NO: 1, respectively. In addition, examples include a consecutive nucleotide sequence of 30 nucleotides in length, which begins at any nucleotide of nucleotide number 650 to 673, 768 to 773, 823 to 867, 902 to 945, 971 to 985, 1021 to 1037, 1070 to 1106, or 1152 to 1180 of the nucleotide sequence of SEQ ID NO: 1, and terminates at any nucleotide of nucleotide number 679 to 702, 797 to 802, 852 to 896, 931 to 974, 1000 to 1014, 1050 to 1066, 1099 to 1135, or 1181 to 1209 of the nucleotide sequence of SEQ ID NO: 1, respectively. In addition, examples include a consecutive nucleotide sequence of 20 nucleotides in length, which begins at any nucleotide of nucleotide number 720, 823, 825, 826, 836, 837, 859, 907, 908, 910, 921, 951, 993, 994, 1004, 1032 or 1082 of the nucleotide sequence of SEQ ID NO: 1, and terminates at any nucleotide of nucleotide number 739, 842, 844, 845, 855, 856, 878, 926, 927, 929, 940, 970, 1012, 1013, 1023, 1051 or 1101 of the nucleotide sequence of SEQ ID NO: 1, respectively. More specifically, it is preferable to select a polynucleotide having nature such as length of sequence and melting point equivalent to that of one or more polynucleotides separately used for detecting a desired gene, from among the above polynucleotides.

In addition, when DNA or RNA is detected using hybridization method such as DNA array analysis or Northern method, it is preferable to use a polynucleotide having a nucleotide sequence which is complementary to a nucleotide sequence represented by any of the aforementioned item number (9) and (10), as shown in the item number (12).

Polynucleotides comprising a nucleotide sequence represented by any of the aforementioned item numbers (9) to (11) can be used alone, or in combination of plural of them. In use of the polynucleotides as a primer in RT-PCR method described later, or as a probe, it is preferable to select a suitable polynucleotide (of 20 to 60 nucleotides, preferably 20 to 50 nucleotides in length) for carrying out a PCR reaction from among polynucleotides having a nucleotide sequence represented by the item number (10) or (11). The selection of the polynucleotide can be performed from the polynucleotides shown above using a commercially available gene analysis software such as DNASIS (manufactured by Hitachi Software). In addition, when a number of polynucleotides detecting different nucleotide sequence regions of gene are used for the purpose of enhancing reliability at detection, it is desirable to use a number of polynucleotides having nucleotide sequences represented by the item number (10) or (11) which are not overlapped with each other.

The present polynucleotide for detecting DNA may be obtained using any method as far as it is a method capable of obtaining this.

For examples, as specifically shown in the item of the present gene or present polynucleotide, the polynucleotide for detecting DNA can be obtained from a tissue of marmoset such as common marmoset or cultured cells derived from the animal using hybridization method or PCR method and, additionally, there is a preferable method of chemically synthesizing the polynucleotide with a commercially available DNA synthesizer based on information of a nucleotide sequence.

Then, the present composition will be explained.

The present composition is a composition for detecting DNA or RNA, and comprises the present polynucleotide. The composition may be in a form where the present polynucleotide is immobilized on a carrier. Of the form, a representative form in which the present polynucleotide is immobilized on a surface of a solid substrate is a DNA array (hereinafter, referred to as the present DNA array in some cases).

Gene expression analysis procedures are extensively utilized in a variety of aspects such as diagnosis, classification or prediction of development of a disease, and mechanism analysis of medicinal property, toxicity or side effect of chemical substance. Although Northern blotting method has been previously utilized in the gene expression analysis procedure, quantitative reverse transcriptase-polymerase chain reaction method (hereinafter, sometimes referred to as quantitative RT-PCR method), and a procedure using a DNA array (hereinafter, referred to as DNA array method in some cases) have been developed, and these procedures are also utilized currently.

In quantitative RT-PCR method, usually, a polynucleotide such as mRNA and total RNA which contains a transcript of a desired gene is extracted and purified separately from a number of test samples. Complementary DNA (cDNA) corresponding to the extracted and purified polynucleotide is synthesized using a reverse transcriptase, and then an amount of the synthesized cDNA is quantitated using PCR method. By comparing relatively amounts of the quantitated cDNA between a number of test samples, a difference in a level of expression of the desired gene is measured. The present composition is useful when the gene expression analysis procedure accompanied with the relative comparison is performed.

In DNA array method, usually, a polynucleotide such as mRNA and total RNA which contains a transcript of a desired gene is extracted and purified separately from a number of test samples. After cDNA corresponding to the extracted and purified polynucleotide or cRNA obtained by subjecting the cDNA to an in vitro transcription reaction is labeled using a fluorescent dye or a radioisotope, the resulting labeled entity is hybridized with a DNA array. An amount of the hybridized labeled entity is quantitated based on a fluorescent intensity or a radiation intensity. By comparing relatively the quantitated cDNA amount or cRNA amount between a number of test samples, a difference in a level of expression of the desired gene is measured. The present composition is useful when the gene expression analysis procedure accompanied with the relative comparison is performed.

A DNA array is roughly classified depending on the number of DNA probes arrayed on a surface of a solid substrate into two kinds of DNA arrays in one of which about a few to a few hundreds of DNA probes are arrayed, and in the other of which the number greater than that number of DNA probes are arrayed, and the present DNA array includes both of them.

The present DNA array contains the present polynucleotide as a probe, and the number of probes and nucleotide sequence thereof other than the present polynucleotide are not particularly limited. Examples include a DNA array containing the present polynucleotide as a probe, and containing a few to a few tens thousands of probes corresponding to genes other than the present gene. Preferable examples include a DNA array containing the present polynucleotide as a probe, and containing a few to a few tens thousands probes corresponding to a gene derived from common marmoset other than the present gene.

The present DNA array can be manufactured by both steps of a step of preparing a DNA probe containing a polynucleotide comprising all or a part of the nucleotide sequence of SEQ ID No: 1 according to a method described, for example, in Genome Function Study Protocol, Experimental Medicine Separate Volume (Published by Yodosha), and a step of immobilizing the prepared DNA probe on a surface of a solid substrate. Alternatively, a DNA array can be also manufactured directly by adding successively nucleotides to a solid substrate and performing chemical synthesis, as described in Fodor, S. P. A. et al., Science, 251, 767 (1991), based on information of a nucleotide sequence possessed by a DNA probe. The former manufacturing method will be explained in more detail below, but a method of manufacturing the present DNA array is not limited thereto.

First, DNA probes are prepared. DNA probes can be prepared by PCR method using, as a template, cDNA prepared from a tissue of common marmoset. By performing PCR using a DNA polymerase such as Ex Taq (Takara Bio Inc.) and using the cDNA as a template, DNA is amplified. The amplified DNA may be cloned by inserting it into a vector such as pUC118. A nucleotide sequence of the DNA can be confirmed using a method according to the aforementioned Maxam Gilbert method or Sanger method.

The DNA amplified by the PCR reaction can be used as a probe.

The DNA amplified by the PCR reaction can be purified by recovering the DNA from a solution containing the DNA by ethanol precipitation. Alternatively, the DNA can be purified using a commercially available DNA purifying column such as QIAquick PCR Purification Kit (manufactured by Qiagen). As a solvent for dissolving the DNA in the purification, dimethyl sulfoxide, water, physiological saline, a suitable buffer such as 1 to 100 mM Tris-HCl, or a solution such as 3×SSC can be used. Preferably, 3×SSC may be used. A concentration of DNA upon dissolution is adjusted to about 1 to about 100 µM. When DNA cloned into a vector is used, an objective DNA is excised with a suitable restriction enzyme, and is purified by an agarose gel, if necessary. The resulting DNA can be separated from the gel using a commercially available DNA purification column such as QIAquick Gel Extraction Kit (manufactured by Qiagen). The DNA separated from the gel is dissolved in the aforementioned solvent. In addition, DNA for a DNA probe may be obtained by performing PCR again using, as a primer, a nucleotide sequence such as T7, T3 and SP6 which is usually set at both termini of a cloning region of a cloning vector.

When a length of DNA arranged on a DNA array is about 20 nucleotides to about 100 nucleotides, examples of a preferable method include chemical synthesis with a commercial available DNA synthesizer based on information of a nucleotide sequence. The chemically-synthesized DNA is purified by the aforementioned DNA purification column or high performance liquid chromatography, and is dissolved in the aforementioned solvent.

Then, the DNA obtained above is immobilized on a carrier such as a solid substrate. Examples of the carrier include a solid substrate such as a glass plate, a quartz plate, a silicon wafer, a membrane filter and the like. Size of a carrier may be appropriately set depending on the number of DNA probes arranged on a carrier, and size of a spot of DNA probe. As a method for immobilizing DNA, a suitable method may be selected depending on a kind of DNA, and a kind of a carrier. For example, when DNA to be immobilized is cDNA, or a PCR amplification product, examples include a method of electrostatic binding to a solid carrier having a surface treated with a polycationic ion such as polylysine, polyethyleneimine and polyalkylamine utilizing a charge of DNA, and a method of covalently binding DNA with a functional group such as an amino group, an aldehyde group, a SH group and biotin on a surface of a solid layer on which a functional group such as an amino group, an aldehyde group and an epoxy group is introduced. For arranging the prepared DNA on a carrier, a method of manually adding dropwise a solution in which the DNA is dissolved using micropipette or a pipetteman or a method of arranging at a position pre-instructed by a size of a few tens µm to a few hundreds µm by a machine procedure may be used. Examples of a method of arranging DNA include a pin system by mechanical contact of a carrier at a pin tip, an ink-jet system utilizing a principle of an ink-jet printer, and a capillary system by a capillary, and any system of them may be used. Examples of the pin system include Affymetrix 427 Arrayer (manufactured by Affymetrix, Inc.), and examples of a capillary system include Lucidea Array Spotter (manufactured by Amersham Biosciences Corp.), being not limiting. An amount of a solution of DNA to be arranged is preferably 0.01 to 100 nl when arranged mechanically, or preferably 0.1 to 100 µl when arranged manually.

The present polynucleotide may be used as an internal standard which can be used to determine a standard of level of gene expression in a test sample for normalizing an amount of a transcript of a desired gene when a difference in levels of expression of the desired gene in two or more kinds of test samples is measured by measuring a difference in amounts of the transcript of the desired gene in said samples. It is better that the test sample is a sample derived from common marmoset.

The present measuring method 1 is a method for measuring a difference in levels of expression of a desired gene in two or more kinds of test samples by measuring a difference in amounts of a transcript of the desired gene in said samples, which comprises:

(1) a first step of measuring an amount of a transcript of a common marmoset-derived glyceraldehyde-3-phosphate dehydrogenase gene in two or more kinds of test samples using the present polynucleotide, (2) a second step of measuring an amount of a transcript of a desired gene in said test samples using a polynucleotide for detecting the desired gene, (3) a third step of normalizing the amount of the transcript of the desired gene measured in the second step in each test sample by using as an internal standard the amount of the transcript of the glyceraldehyde-3-phosphate dehydrogenase gene measured in the first step in said test sample, and (4) a fourth step of comparing the normalized amounts of the transcript of the desired gene in two or more kinds of test samples, thereby measuring a difference in the relative amounts of the transcript of the desired gene in the test samples.

The present measuring method 2 is a method for measuring a difference in levels of expression of a desired gene in two or more kinds of test samples by measuring a difference in amounts of a transcript of the desired gene in said samples, which comprises:

(1) a first step of measuring an amount of a transcript of a common marmoset-derived glyceraldehyde-3-phosphate dehydrogenase gene in two or more kinds of test samples using the present polynucleotide, (2) a second step of measuring an amount of a transcript of a desired gene in said test samples using a polynucleotide for detecting the desired gene, (3) a third step of calculating an inverse of the ratio of the amount of the transcript of the glyceraldehyde-3-phosphate dehydrogenase gene measured in the first step in a test sample relative to the amount of the transcript of the glyceraldehyde-3-phosphate dehydrogenase gene measured in the first step in a test sample to be a standard, (4) a fourth step of normalizing the amounts of the transcript of the desired gene measured in the second step in the test samples by multiplying the amount of the transcript of the desired gene measured in the second step in each test sample with the inverse of the ratio calculated in the third step for said test sample, and (5) a fifth step of comparing the normalized amounts of the transcript of the desired gene in two or more kinds of test samples, thereby measuring a difference in the relative amounts of the transcript of the desired gene in the test samples.

The present measuring method 3 is a method for measuring a difference in levels of expression of a desired gene in two or more kinds of test samples by measuring a difference in amounts of a transcript of the desired gene in said samples, which comprises:

(1) a first step of measuring an amount of a transcript of a common marmoset-derived glyceraldehyde-3-phosphate dehydrogenase gene in two or more kinds of test samples using the present polynucleotide,
(2) a second step of measuring an amount of a transcript of a desired gene in said test samples using a polynucleotide for detecting the desired gene,
(3) a third step of normalizing the amount of the transcript of the desired gene measured in the second step in the test samples by calculating the ratio of the amount of the transcript of the desired gene measured in the second step in each test sample relative to the amount of the transcript of the glyceraldehyde-3-phosphate dehydrogenase gene measured in the first step in said test sample, and
(4) a fourth step of comparing the normalized amounts of the transcript of the desired gene in two or more kinds of test samples, thereby measuring a difference in the relative amounts of the transcript of the desired gene in the test samples. Hereinafter, the present measuring method 1 to 3 may be collectively referred to as the present measuring method.

In the present measuring method, it is better that the test sample is a common marmoset-derived sample.

As a method of measuring an amount of a transcript of a gene in a first step and a second step in the present measuring method, any method may be used as far as it is a method capable of quantitatively measuring an amount of a transcript, and examples include Northern hybridization method [Sambrook, J. et al., Molecular Cloning: A laboratory Manual 3rd edition, Cold Spring Harbor Laboratory Press (2001)], quantitative RT-PCR method, DNA array method, and in situ hybridization method. Preferable examples include any method of DNA array method and quantitative reverse transcriptase-polymerase chain reaction method.

(1) Northern Hybridization Method

First, DNA corresponding to a nucleotide sequence of a desired gene to be analyzed is prepared, and DNA consisting of all or a part of it is labeled to prepare a labeled probe. As used herein, the "labeled DNA probe" is DNA labeled with a fluorescent dye or a radio isotope, which hybridizes specifically with a gene having a particular nucleotide sequence, and is used for the purpose of measuring the presence or the absence of expression of the gene and a level of its expression. In addition, also regarding the present gene or the present polynucleotide, DNA thereof is similarly labeled to prepare a labeled probe. A desired gene can be prepared by PCR using, as a template, cDNA prepared from a tissue of common marmoset by the aforementioned method. DNA is amplified by performing PCR using, as a template, the cDNA, and using a DNA polymerase such as Ex Taq (Takara Bio Inc.). Condition of the PCR is different depending on a kind of a desired gene, and a nucleotide sequence of primers to be used, and examples include the aforementioned reaction condition. The amplified DNA may be cloned by inserting into a pUC118 vector and the like. A nucleotide sequence of the DNA can be confirmed using a method according to the aforementioned Maxam Gilbert method, or Sanger method.

The prepared DNA of a desired gene, and the present gene or the present polynucleotide are labeled with a fluorescent dye or a radioisotope as follows, thereby, a probe can be prepared. For example, by using the prepared DNA as a template, and using an oligonucleotide having a partial sequence of a nucleotide sequence of the DNA as a primer, and performing PCR by adding dNTP containing [$\alpha$-$^{32}$P] dCTP or [$\alpha$-$^{32}$P]dATP to a reaction solution, a probe labeled with $^{32}$P is obtained. Alternatively, the prepared DNA may be labeled using a commercially available labeling kit such as Random prime labeling Kit (Roche Diagnostic), and MEGA-LABEL (Takara Bio Inc.).

Then, using the prepared probe, Northern hybridization analysis is performed. Specifically, in a second step of the present measuring method, total RNA or mRNA is prepared from two or more kinds of test samples derived from common marmoset for which an amount of a transcript of a desired gene is to be measured. 20 μg of the prepared total RNA or 2 μg of the mRNA is separated by an agarose gel, the gel is washed with 10×SSC (1.5M Nacl, 0.35M sodium citrate), and the separated RNA is transferred to a nylon membrane [e.g. Hybond-N (manufactured by Amersham Biosciences Corp.)] from the gel. The membrane is placed into a polyethylene bag, 25 ml of a hybridization buffer [6×SSC (0.9 M NaCl, 0.21M sodium citrate), and 5× Denhart solution [0.1% (w/v) Ficoll 400, 0.1% (w/v) polyvinylpyrrolidone, 0.1% BSA], 0.1% (w/v) SDS, 100 μg/ml denatured salmon sperm DNA, 50% formamide] is added into the bag. After the bag is incubated at 50° C. for 2 hours, the hybridization buffer is discarded, and 2 ml to 6 ml of a hybridization buffer is newly added. Further, a labeling probe obtained by the aforementioned method is added, and this is incubated at 50° C. overnight. As a hybridization buffer, in addition to the aforementioned buffer, commercially available DIG easy Hyb (Roche Diagnostic) can be used. The membrane is removed, and incubated at room temperature for 15 minutes in 50 ml to 100 ml of 2×SSC, 0.1% SDS, the same procedure is repeated once and, finally, the membrane is incubated at 68° C. for 30 minutes in 50 ml to 100 ml of 0.1×SSC, 0.1% SDS. By measuring an amount of a label on the membrane, an amount of a transcript of the desired gene can be measured.

Separately, total RNA or mRNA prepared from the same test sample is separated using an agarose gel by the aforementioned method, and is transferred to a nylon membrane. A labeled probe corresponding to the present gene or the present polynucleotide which was obtained by the aforementioned method is added, hybridization is performed according to the aforementioned condition, and an amount of a label on the membrane is measured, thereby, an amount of a transcript of the present gene can be measured.

Alternatively, other than separately preparing a nylon membrane to which total RNA or mRNA has been transferred, the labeled probe is removed from the nylon membrane for which an amount of a transcript of a desired gene has been measured, and an amount of a transcript of the present gene can be measured using the resulting membrane. In this case, for example, by warming or boiling the membrane for 5 to 30 minutes in a solution containing 0.1 to 1% SDS, the hybridized labeled probe is removed. After the nylon membrane is returned to room temperature, hybridization is performed with a labeled probe corresponding to the present gene or the present polynucleotide under the aforementioned condition, thereby, an amount of a transcript of the present gene can be measured.

(2) Quantitative RT-PCR

By a method similar to the method described in the (1) Northern hybridization method, mRNA is prepared from two or more kinds of test samples derived from common marmoset for which an amount of a transcript of a desired gene is to be analyzed. By adding a reverse transcriptase such as MMLV (Toyobo Co., Ltd.) to the prepared mRNA, to react them at 42° C. for 15 minutes to 1 hour in a reaction buffer [50 mM Tris-HCl buffer (pH 8.3), 3 mM $MgCl_2$, 75 mM KCl, 10 mM DTT] in the presence of 0.5 mM dNTP and 25 µ/ml oligo dT, cDNA corresponding to the mRNA is prepared. The corresponding cDNA may also be prepared using a cDNA synthesis kit (Takara Bio Inc.).

PCR is performed using the prepared cDNA as a template, and using DNA comprising a part of a nucleotide sequence of a desired gene as a primer. A primer used in the PCR may be designed using a commercially available gene analysis software such as DNASIS (manufactured by Hitachi Software). For example, a primer hardly forming an unnecessary secondary structure and having a nucleotide sequence having high specificity for the gene, which is an oligonucleotide of about 15 nucleotides to about 50 nucleotides in length can be used. As a condition for the PCR, examples include the condition under which 25 to 55 cycles of incubation are performed, one cycle consisting of incubation at 95° C. for 30 seconds, then, at 40° C. to 60° C. for 2 minutes and, further, at 72° C. for 2 minutes in a reaction buffer [10 mM Tris-HCl buffer (pH 8.3), 50 mM KCl, 1.5 mM $MgCl_2$] in the presence of 2.5 mM dNTP and $[\alpha^3\ ^2P]$-dCTP using Ex taq (Takara Bio Inc.). The amplified DNA is subjected to polyacrylamide gel electrophoresis, and radiation intensity of the separated DNA is measured, thereby, an amount of a transcript of the gene can be measured.

Alternatively, for example, PCR is performed at the condition under which Ex taq (Takara Bio Inc.) is used in 50 µl of a reaction solution containing 25 µl of SYBR Green PCR Reagents (Applied Biosystems) in a reaction buffer [10 mM Tris hydrochloric acid buffer (pH 8.3), 50 mM KCl, 1.5 mM $MgCl_2$]. The reaction solution is incubated at 50° C. for 2 minutes, then, at 95° C. for 10 minutes, followed by 40 cycles of incubation, one cycle consisting of incubation at $_{95}$° C. for 15 seconds and, then, at 65° C. for 1 minute using ABI7700 (Applied Biosystems). By measuring fluorescent intensity of the amplified DNA, an amount of a transcript of the gene can be measured.

In addition, using the cDNA as a template, and using the present polypeptide as a primer, PCR is performed. The PCR may be performed at the same time with, or at a different time from, preferable at the same time with PCR for the purpose of measuring an amount of a transcript of a desired gene.

A primer used in the PCR maybe designed using a commercially available gene analysis software such as DNASIS (manufactured by Hitachi Software). For example, a primer hardly forming an unnecessary secondary structure and having a nucleotide sequence having a high specificity for the gene, which is an oligonucleotide of about 15 nucleotides to about 50 nucleotides in length can be used. Condition for the PCR is preferably the same condition as the condition used for measuring an amount of a transcript of a desired gene. Examples include condition under which Ex taq (Takara Bio Inc.) is used, and 25 to 55 cycles of incubation are performed, one cycle consisting of incubation at 94° C. for 30 seconds, then, at 40° C. to 60° C. for 2 minutes and, further, at 72° C. for 2 minutes in a reaction buffer [10 mM Tris hydrochloric acid buffer (pH 8.3), 50 mM KCl, 1.5 mM $MgCl_2$] in the presence of 2.5 mM dNTP and $[\alpha^3\ ^2P]$-dCTP. By subjecting the amplified DNA to polyacrylamide gel electrophoresis, and measuring a radiation intensity of the separated DNA, an amount of a transcript of the present gene can be measured. Alternatively, PCR is performed at the condition under which Ex taq (Takara Bio Inc.) is used in 50 µl of a reaction solution containing 25 µl of SYBR Green PCR Reagents (Applied Biosystems) in a reaction buffer [10 mM Tris hydrochloric acid buffer (pH 8.3), 50 mMKCl, 1.5 mM$MgCl_2$]. The reaction solution is incubated at 50° C. for 2 minutes, then, at 95° C. for 10 minutes, followed by 40 cycles of incubation, one cycle consisting of incubation at 95° C. for 15 seconds and, then, at 65° C. for 1 minute using ABI7700 (Applied Biosystems). By measuring fluorescent intensity of the amplified DNA, an amount of a transcript of the present gene can be measured.

(3) DNA Array Analysis

In order to measure an amount of a transcript of a desired gene to be analyzed and an amount of a transcript of the present gene in a test sample, measurement may be performed using a DNA array according to conventional techniques. Such the DNA array is such that a few tens to a few tens thousands DNA probes are arranged on a surface of a solid substrate such as a membrane filter and a slide glass in an array arrangement. By using this, the presence or the absence of expression of a desired gene in a test sample and a level of expression thereof can be investigated at once. A DNA probe used herein is DNA which specifically hybridizes with a gene having a particular nucleotide sequence, and is used for the purpose of measuring the presence or the absence of expression of the gene and a level of expression thereof, like those used in the (1) Northern hybridization method. A DNA array is roughly classified depending on the number of DNA probes arrayed on a surface of a solid substrate into two kinds of DNA arrays in one of which about a few to a few hundreds of DNA probes are arrayed, and in the other of which the number greater than that number of DNA probes are arrayed, and both are included herein.

A DNA array used in the present invention can be prepared according to the method described, for example, in Genome Function Study Protocol, Experimental Medicine Separate Volume (published by Yodosha). Alternatively, a DNA array can be also manufactured directly by adding successively nucleotides to a solid substrate to perform chemical synthesis, as described in Fodor, S. P. A. et al., Science, 251, 767 (1991), based on information of a nucleotide sequence possessed by a DNA probe. Details of a process for preparing a DNA array is as described above.

One example of a method for measuring an amount of a transcript of the present gene using a DNA array will be shown below.

(3-1) Quantitation with a DNA Microarray (1)

By a method similar to the method described in the (1) Northern hybridization method, mRNA is prepared from a test sample for which an amount of a transcript of a desired gene is to be analyzed. A reverse transcriptase such as MMTV (Toyobo Co., Ltd.) is added to the prepared mRNA, to react them at 42° C. for 15 minutes to 1 hour in a reaction buffer [e.g. a solution containing 50 mM Tris-HCl buffer (pH 8.3), 3 mM $MgCl_2$, 75 mM KCl and 10 mM DTT] in the presence of 0.5 mM dNTP, $[\alpha^{32}\ ^P]$-dCTP, and 25 µg/ml oligo dT, whereby, labeled cDNA is prepared. Thereupon, a cDNA synthesizing kit (Takara Bio Inc.) maybe used. A DNA array prepared by spotting, on a membrane filter, DNA probes having separate nucleotide sequences each consistent with all or a part of a nucleotide sequence of a desired gene to be analyzed, the present gene or the present full length cDNA is placed in a polyethylene bag, 25 ml of a hybridization buffer [6×SSC (0.9M NaCl, 0.21 m sodium citrate), 5× Denhart solution [0.1% (w/v) Ficoll400, 0.1% (w/v) polyvinylpyrrolidone, 0.1% BSA, 0.1% (w/v) SDS, 100 µg/ml denatured salmon sperm DNA, 50% formamide] is added, this is incubated at 50° C. for 2 hours, the hybridization buffer is removed, and 2 ml to 6 ml of a hybridization buffer is newly added. Further, to this is added the aforementioned labeled cDNA, and this is incubated at 50° C. overnight. As a hybridization buffer, in addition to the aforementioned buffer, commercially available DIG EASY Hyb (Roche Diagnostic) may be used. After the hybridization, the DNA array is removed, immersed in 50 ml to 100 ml of 2×SSC, 0.1% SDS, and incubated at room temperature for about 15 minutes. Further, the same procedure is repeated once and, finally, incubation is performed at 68° C. for 30 minutes in 50 ml to 100 ml of 0.1×SSC, 0.1% SDS. Then, by measuring an amount of label on the DNA array, an amount of transcripts of the desired gene to be analyzed and the present gene can be measured.

(3-2) Quantitation with a DNA Microarray (2)

By a method similar to the method described in the (1) Northern hybridization method, mRNA is prepared from a test sample for which an amount of a transcript of a desired gene is to be analyzed. A reverse transcriptase such as MMTV (Toyobo Co., Ltd.) is added to the prepared mRNA, to react them at 42° C. for 15 minutes to 1 hour in a reaction buffer [e.g. a solution containing 50 mM Tris-HCl buffer (pH 8.3), 3 mM $MgCl_2$, 75 mM KCl and 10 mM DTT] in the presence of 0.5 mM dNTP, Cy3-dUTP (or Cy5-dUTP) and 25 µg/ml oligo dT. To the reaction solution is added an alkali buffer (e.g. a solution containing 1N NaOH, 20 mM EDTA), this is incubated at 65° C. for 10 minutes, and free Cy3 or Cy5 is removed using Qiaquick PCR Purification kit (Qiagen), thereby, fluorescently labeled DNA is prepared. The prepared fluorescently labeled DNA is hybridized with a DNA array by a method similar to the method described in the (3-1) Quantitation with DNA array (1). By measuring an amount of label on the DNA array with a scanner, an amount of transcripts of a desired gene to be analyzed and the present gene can be measured.

(4) In Situ Hybridization Method

Fundamentally, an in situ hybridization method comprises (a) fixation and embedding of a tissue, and preparation of a section, (b) preparation of a probe, and (c) detection by hybridization, and can be performed according to the method described, for example, in Heiles, H. et al., Biotechniques, 6, 978, 1988; Genetic Technology Handbook, Yodosha 278 1001; Cell Technology Handbook, Yodosha, 214, 1992; or Cell Technology Handbook, Yodosha, 222, 1992 except that RNA or DNA pre-labeled with radioactive or non-radioactive substance is used as a probe.

When a RNA probe is prepared, first, a desired gene to be analyzed and the present gene or a full length cDNA is obtained by a method similar to the method described in the (1) Northern hybridization method, and the DNA is inserted into a vector having SP6, T7 or T3 RNA polymerase promoter (e.g. Bluescript of Strategene, pGEM of Promega etc.), which is introduced into *Escherichia coli*, thereby, plasmid DNA is prepared. Then, the plasmid DNA is cut with restriction enzymes so that a sense (for negative control) RNA and an antisense (for hybridization) can be prepared. Using either of the plasmid DNA as a template, and using $\alpha$-$^{35}$S-UTP in the case of a radioactive label, or digoxigenine UTP or fluorescein-modified UTP in the case of a non-radioactive label as a substrate, RNA is labeled while it is synthesized, using SP6, T7 or T3 RNA polymerase. The labeled RNA is cut into a suitable size for hybridization by alkali hydrolysis, thereby, RNA pre-labeled with a radioactive or non-radioactive substance is prepared. As a kit based on these methods, for example, a RNA labeling kit (Amersham Biosciences Corp.) is commercially available for a radioactive label, and DIG RNA labeling kit (Roche Diagnostic) and RNA color kit (Amersham Biosciences Corp.) are commercially available for a non-radioactive label. In addition, when a DNA probe is prepared, for example, by incorporation of a radio active nucleotide labeled with $^{32}$P, or a nucleotide labeled with biotin, digoxigenine or fluorescein by a nick translation method [Sambrook, J. et al., Molecular Cloning: A laboratory Manual 3rd edition, Cold Spring Harbor Laboratory Press (2001)], or a random priming [Feinberg, A. P., B. Vogelstein, Anal. Biochem., 132, 6 (1083), Feinberg, A. P., B. Vogelstein, Anal. Biochem., 137, 266 (1984)], DNA pre-labeled with a radioactive or non-radioactive substance is prepared. As a kit based on these methods, for example, a nick translation kit (Amersham Biosciences Corp.), and Random Prime Labeling Kit (Roche Diagnostic) are commercially available for a radioactive label, and DIG DNA labeling kit (Roche Diagnostic), and DNA color kit (Amersham Biosciences Corp.) are commercially available for a non-radioactive label.

Specifically, a test sample for which an amount of transcripts of a desired gene is to be analyzed and the present gene is fixed with paraformaldehyde, and embedded in paraffin, a thin section is prepared, and this is attached to a slide glass. In addition, the test sample is frozen in liquid nitrogen, a fine thin layer section is prepared, and this is attached to a slide glass. Like this, a slide glass section is obtained.

Then, in order to remove a substance which is present in the test sample and non-specifically reacts with a probe to be used, a slide glass section prepared as described above is treated with proteinase K, and is acetylated. Then, the slide glass section and the probe prepared as described above are hybridized. For example, the probe is heated at 90° C. for 3 minutes, and then diluted with a hybridization solution to obtain a solution, which is added dropwise on the slide glass section. After addition dropwise, the slide glass section is covered with a film, and incubated at 45° C. for 16 hours in a moisture chamber, thereby, a hybrid is formed. After hybridization, a non-specifically adsorbed or unreacted probe is washed (when a RNA probe is used, RNase treatment is added) to remove it. By measuring an amount of a label on the slide glass section, an amount of transcripts of a desired gene to be analyzed and the present gene can be measured.

In a third step of the present measuring method 1, the amount of the transcript of the desired gene measured in the second step in each test sample is normalized by using as an internal standard the amount of the transcript of the glyceraldehyde-3-phosphate dehydrogenase gene measured in the first step in said test sample. Then, in a fourth step of of the present measuring method 1, the normalized amounts of the transcript of the desired gene in two or more kinds of test samples are compared, thereby a difference in the relative amounts of the transcript of the desired gene in the test samples is measured.

In a third step in the present measuring method 2, among two or more kinds of test samples, an inverse of the ratio of the amount of the transcript of the glyceraldehyde-3-phosphate dehydrogenase gene measured in the first step in a test sample relative to the amount of the transcript of the glyceraldehyde-3-phosphate dehydrogenase gene measured in the first step in a test sample to be a standard is calculated.

Specifically, for example, letting the number of measured test samples to be n, letting an amount of a transcript of a common marmoset-derived glyceraldehyde-3-phosphate dehydrogenase gene in a $x^{th}$ ($x \leq n$) test sample to be Sx, and letting an amount of a transcript of a common marmoset-derived glyceraldehyde-3-phosphate dehydrogenase gene in an $i^{th}$ ($i \leq n$) test sample to be Si, when calculation is performed using the Si as a standard, an inverse of a relative ratio Cx is expressed by the following equation.

$$Cx = Si/Sx$$

Herein, the "test sample to be a standard" may be any test sample among measured test samples, and it is preferable to use it when a control test sample is used for measurement.

In a fourth step in the present measuring method 2, the amounts of the transcript of the desired gene measured in the second step in the test samples are normalized by multiplying the amount of the transcript of the desired gene measured in the second step in each test sample with the inverse of the ratio calculated in the third step for said test sample.

Specifically, for example, letting the number of measured test samples to be n, letting an amount of a transcript of a desired gene to be analyzed in a $x^{th}$ ($x \leq n$) test sample to be Tx, letting the inverse of a relative ratio of an amount of a transcript of a common marmoset-derived glyceraldehyde-3-phosphate dehydrogenase gene in a $x^{th}$ test sample relative to an $i^{th}$ ($i \leq n$) test sample calculated by the third step to be Cx, when calculation is performed using, as a standard, an amount of a transcript of an $i^{th}$ test sample glyceraldehyde-3-phosphate dehydrogenase gene is performed, an amount ATx of a transcript of a desired gene to be analyzed which has been normalized by the step is expressed by the following equation.

$$ATx = Tx \times Cx$$

In a fifth step in the present measuring method 2, the normalized amounts of the transcript of the desired gene in two or more kinds of test samples are compared, thereby a difference in the relative amounts of the transcript of the desired gene in the test samples is measured.

In a third step in the present measuring method 3, the amount of the transcript of the desired gene measured in the second step in the test samples is normalized by calculating the ratio of the amount of the transcript of the desired gene measured in the second step in each test sample relative to the amount of the transcript of the glyceraldehyde-3-phosphate dehydrogenase gene measured in the first step in said test sample.

In a fourth step in the present measuring method 3, the normalized amounts of the transcript of the desired gene in two or more kinds of test samples are compared, thereby a difference in the relative amounts of the transcript of the desired gene in the test samples is measured.

EXAMPLES

The present invention will be explained in more detail by the following examples, but the present invention is not limited to these particular Examples.

Example 1

(Cloning of Common Marmoset glyceraldehyde-3-Phosphate Dehydrogenase Gene)

(1) Preparation of total RNA

Total RNA was extracted from a liver of a common marmoset (obtained from Clea Japan, Inc.).

Forty-seven (47) months-old male common marmoset was sacrificed to isolate a liver. The isolated liver was cut into pieces using tweezers and scissors, immediately immersed in RNAlater (Ambion, Inc.), left at room temperature overnight, and stored at −20° C. until just before use. Ten (10) ml of a TRIZOL reagent (manufactured by Invitrogen Corp.) was added to 1 g wet weight of the stored liver tissue, and the tissue was homogenized with a Polytron homogenizer while kept on ice, and left at room temperature for 5 minutes. Then, the obtained homogenate was centrifuged (4° C., 9,000 rpm, 10 minutes), and the aqueous layer was collected in a 50 ml volume of centrifugation tube (manufactured by Asahi Techno glass Corp.). After one fifth the TRIZOL reagent volume of chloroform (manufactured by Kanto Kagaku) was added to the collected aqueous layer, the resulting mixture was vigorously shaken for 15 seconds, and left at room temperature for 5 minutes. Then, the mixture was centrifuged (4° C., 9,000 rpm, 10 minutes) to collect the aqueous layer in a 50 ml volume of new centrifugation tube. One-half the TRIZOL reagent volume of 2-propanol (manufactured by Kanto Kagaku) was added to the collected aqueous layer. The resulting mixture was mixed by inverting the tube, and left at room temperature for 10 minutes. Then, the mixture was centrifuged (4° C., 9,000 rpm, 10 minutes), and the supernatant was removed to obtain a pellet of RNA. The resulting pellet was dissolved in 1 ml of DEPC-treated sterile distilled water (manufactured by Nacalai Tesque, Inc.). To 1 ml of the obtained RNA solution was added 3.8 ml of RLT buffer (10 µl β-mercaptoethanol/mL RLT buffer) provided in RNeasy Midi Kit (manufactured by Qiagen), and mixed. Further, 2.8 ml of ethanol (manufactured by Kanto Kagaku) was added to the mixture, followed by mixing. After the mixture was divided into equivalent amounts, each was applied to a RNeasy Spin Column provided in RNeasy Midi Kit, and centrifuged (room temperature, 10,000 rpm, 15 seconds). After centrifugation, each eluant was applied to the same RNeasy Spin Column again, and centrifuged (room temperature, 10,000 rpm, 15 seconds). After centrifugation, each eluant was discarded, each 2.5 ml of RPE buffer (provided in RNeasy Midi Kit) diluted 4-fold with ethanol was applied, and each was centrifuged (room temperature, 10,000 rpm, 15 seconds). After centrifugation, each eluant was discarded again, each 2.5 ml of RPE buffer diluted with ethanol was applied, and each was centrifuged (room temperature, 14,000 rpm, 2 minutes). After centrifugation, each column was transferred to an Eppendorf tube, 0.25 ml of distilled water provided in RNeasyMidi Kit was added, and left at room temperature for 1 minute. Then, each was centrifuged (room temperature, 10,000 rpm, 1 minute), thereby, total RNA as each eluant thereof was obtained and combined.

(2) Preparation of cDNA

Twenty (20) µl of a mixture containing 6 µg of the total RNA prepared in the above (1) and 1 µg of a primer having the nucleotide sequence of SEQ ID NO: 5 was heated at 70° C. for 10 minutes, and kept on ice. After cooling, to the mixture were added 8 µl of 5×First Strand cDNA Buffer contained in Super-Script II Choice System for cDNA Synthesis (manufactured by Invitrogen Corp.), 4 µl of 0.1 M DTT contained in the kit, 2 µl of 10 mM dNTP Mix contained in the kit, and 2 µl of Super Script II RT contained in the kit. The mixture was heated at 37° C. for 2 hour, then heated at 75° C. for 5 minutes, and then kept on ice, thereby, cDNA solution was obtained. The obtained cDNA solution was stored at −20° C. until use.

(3) Amplification of the Present Gene by PCR

By conducting PCR using the cDNAs obtained above as a template, and using a forward primer having the nucleotide sequence of SEQ ID NO: 3, a reverse primer having the nucleotide sequence of SEQ ID NO: 6 and Ex Taq polymerase (manufactured by Takara Bio Inc.), DNAs were amplified. The reaction solution used for the PCR was composed of 1 µl of the aforementioned cDNA solution, 5 µl of 10×PCR buffer attached to the Ex taq polymerase, 4 µl of 2.5 mM dNTP attached to the Ex taq polymerase, each 1 µl of the aforementioned primers having a concentration of 10 µl, 0.5 µl of the Ex Taq polymerase, and 37.5 µl of sterile purified water. The PCR was conducted at the following reaction condition: maintaining 94° C. for 2 minutes, followed by repeating 30 cycles of a cycle that included maintaining 94° C. for 30 seconds, then, 60° C. for 30 seconds, and then, 72° C. for 1 minute. Further, the reaction mixture was incubated at 72° C. for 5 minutes, and stored at 4° C. Fifty (50) μl collected from the reaction mixture was subjected to agalose gel electrophoresis. DNA showing on the gel mobility corresponding to that of the amplified DNA was purified using Qiaquick PCR Purification Kit (manufactured by Qiagen), and was collected in 30 μl of sterile purified water.

(4) Preparation of a Clone of the Present Gene

The amplified DNA obtained in the above (3) was cloned using a TA vector.

One (1) μl of the solution containing the amplified DNA and 1 μl of 50 mg/ml pGEM-T vector (manufactured by Promega Corp.) were mixed, and both were ligated using a DNA ligation kit Ver. 2 (manufactured by Takara Bio Inc.). The resulting reaction solution was used to transform *Escherichia coli* DH5α competent cells. Colonies showing ampicillin resistance and a lack of X-gal staining property for beta-galactosidase in the presence of IPTG were isolated. Plasmid DNAs were prepared from the isolated colonies. A nucleotide sequence of the prepared plasmid DNA was analyzed using an automatic DNA sequencer (ABI Model 3700 manufactured by Apllied Biosystems) by dye terminator labeling method. As primers for sequencing, an oligonucleotide having the nucleotide sequence of SEQ ID NO: 7 and an oligonucleotide having the nucleotide sequence of SEQ ID NO: 8 which had been synthesized with a DNA synthesizing apparatus were used. By editing and aligning data of the resulting nucleotide sequences using a DNA sequence analyzing software (DNASIS manufactured by Hitachi Software), the nucleotide sequence of SEQ ID NO: 1 was obtained. The obtained nucleotide sequence was subjected to homology search through NCBI nucleotide databases using the BLAST program. It was found out that the obtained sequence has a high degree homology to a nucleotide sequence of a human glyceraldehyde-3-phosphate dehydrogenase mRNA (accession number NM_002046). Thus, it was confirmed that the obtained sequence was a nucleotide sequence of a common marmoset-derived glyceraldehyde-3-phosphate dehydrogenase gene.

(5 Confirmation of Expression of the Present Gene using RT-PCR Method

In order to analyze an amount of a transcript of a common marmoset-derived glyceraldehyde-3-phosphate dehydrogenase gene obtained in the above (4) in each tissue, RNA was extracted from different individuals and various kinds of tissues, and expression of mRNA was investigated using RT-PCR method.

Tissues were isolated from four 47 to 132 months-old common marmosets (obtained from Clea Japan, Inc.), and total RNA was extracted from each of the tissues using the method described in the above (1). An extracted tissues were 12 kinds of liver, lung, heart, skeletal muscle, brain and kidney (forgoing is from individual number 1), liver, heart and skeletal muscle (forgoing is from individual number 2), liver and lung (forgoing is from individual number 3), and brain (forgoing is from individual number 4). Then, 12 μl of the mixture containing each 1 μg of the total RNAs, and 1 μg of a $d(T)_{12-18}$ primer (manufactured by Amersham Biosciences Corp.) was heated at 70° C. for 10 minutes, and kept on ice. To the mixture were added 4 μl of 5×First Strand cDNA Buffer contained in SuperScript II Choice System for cDNA Synthesis (manufactured by Invitrogen Corp.), 2 μl of 0.1 M DTT contained in the kit, 1 μl of 10 mM dNTPMix contained in the kit, and 1 μl of Super ScriptII RT contained in the kit. The mixture was heated at 42° C. for 60 minutes, further heated at 75° C. for 15 minutes, and then kept at 4° C., thereby, cDNA solution was obtained.

Eighty (80) μl of purified water was added to the obtained cDNA solution to dilute, and this was stored at −20° C. until use. RT-PCR was conducted using the obtained cDNAs as a template, and using a forward primer having the nucleotide sequence of SEQ ID NO: 9 a reverse primer having the nucleotide sequence of SEQ ID NO: 10 and Ex Taq polymerase (manufactured by Takara Bio Inc.). The reaction solution for the RT-PCR was composed of 3 μl of the cDNA solution after the aforementioned dilution, 3 μl of 10×PCR buffer attached to the Ex taq polymerase, 2.4 μl of 2.5 mM dNTP attached to the Ex taq polymerase, each 0.6 μl of the aforementioned primers having a concentration of 10 μM, 0.5 μl of the Extaq polymerase and 22.6 μl of sterile purified water. The PCR was conducted at the following reaction: maintaining 94° C. for 2 minutes, followed by repeating 30 cycles of a cycle that included maintaining 94° C. for 30 seconds, then, 60° C. for 30 seconds, and then, 72° C. for 1 minute. Further, the reaction mixture was incubated at 72° C. for 5 minutes, and stored at 4° C. Three (3) μl collected from the reaction mixture was subjected to agarose gel electrophoresis containing ethidium bromide.

Figure 1:
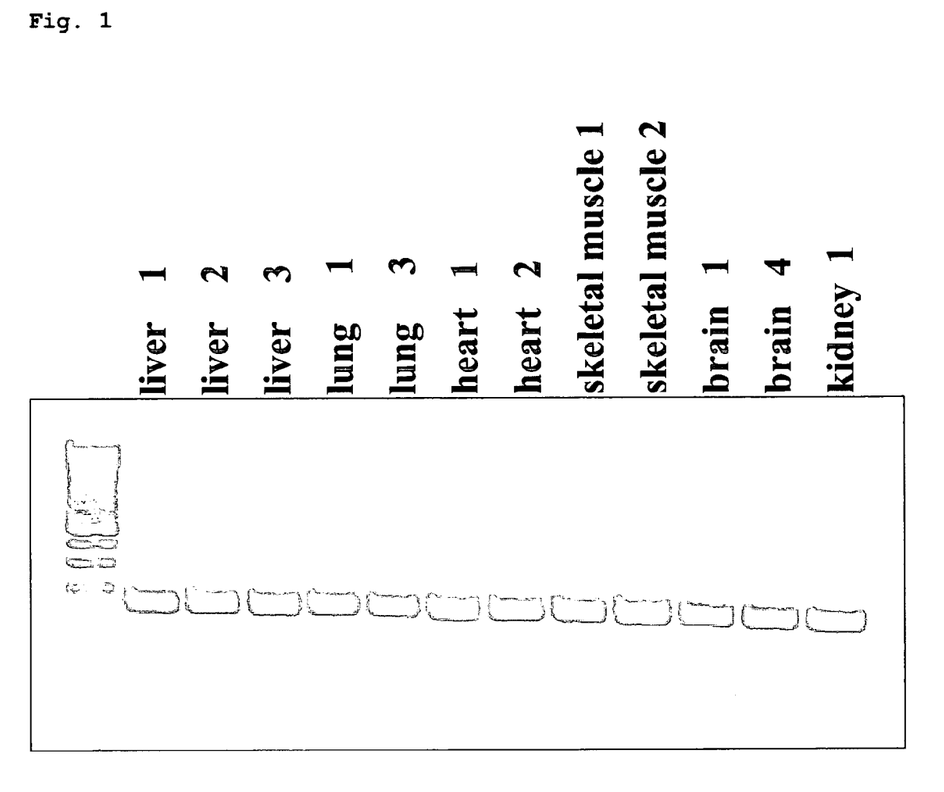
FIG. 1 is an agarose gel showing results of RT-PCR exhibiting expression of a common marmoset-derived glyceraldehyde-3-phosphate dehydrogenase gene in each tissue of common marmoset. In the figure, "1", "2", "3", "4" indicate an individual number from which each tissue was isolated (Example 1(5)).

As a result, as shown in FIG. 1, a band emitting equivalent intensity of fluorescence was detected in 12 kinds of samples which had been subjected to the electrophoresis. From this result, it was confirmed that an approximately same amount of a glyceraldehyde-3-phosphate dehydrogenase gene mRNA was contained in all 12 kinds of tissues which had been subjected to the electrophoresis, regardless of a kind of individuals and tissues.

What is claimed is:

1. An isolated polynucleotide comprising a nucleotide sequence selected from the group consisting of:
   (1) the nucleotide sequence of SEQ ID NO: 1;
   (2) a nucleotide sequence encoding an amino acid sequence of a variant of SEQ ID NO: 2, wherein said variant is SEQ ID NO: 2 having glyceraldehyde 3-phosphate dehydrogenase activity and having one inserted, deleted or conservatively substituted amino acid;
   (3) a nucleotide sequence encoding the amino acid sequence of SEQ ID NO: 2;
   (4) a nucleotide sequence of DNA which has any of the nucleotide sequences as defined in (1) to (3), and is fully complementary to a mature mRNA containing a region from a 5' cap to a poly(A) sequence; and
   (5) a nucleotide sequence which is fully complementary to any of the nucleotide sequences as defined in (1) to (4).

2. A composition for detecting DNA or RNA, which comprises a polynucleotide of claim 1.

3. The composition according to claim 2, wherein said polynucleotide is immobilized on a carrier.

4. A method for measuring a difference in levels of expression of a desired gene in two or more kinds of test samples by measuring a difference in amounts of a transcript of the desired gene in said samples, which comprises:
   (1) measuring an amount of a transcript of a common marmoset-derived glyceraldehyde-3-phosphate dehydrogenase gene in two or more kinds of test samples using a polynucleotide of claim 1,
   (2) measuring an amount of a transcript of a desired gene in said test samples using a polynucleotide for detecting the desired gene,
   (3) normalizing the amount of the transcript of the desired gene measured in (2) in each test sample by using as an internal standard the amount of the transcript of the glyceraldehyde-3-phosphate dehydrogenase gene measured in (1) in said test sample, and (4) comparing the normalized amounts of the transcript of the desired gene in two or more kinds of test samples, thereby measuring a difference in the relative amounts of the transcript of the desired gene in the test samples.

5. The method according to claim 4, wherein said test samples are samples derived from common marmoset.

6. A method for measuring a difference in levels of expression of a desired gene in two or more kinds of test samples by measuring a difference in amounts of a transcript of the desired gene in said samples, which comprises:
   (1) measuring an amount of a transcript of a common marmoset-derived glyceraldehyde-3-phosphate dehydrogenase gene in two or more kinds of test samples using a polynucleotide of claim 1,
   (2) measuring an amount of a transcript of a desired gene in said test samples using a polynucleotide for detecting the desired gene,
   (3) calculating an inverse of the ratio of the amount of the transcript of the glyceraldehyde-3-phosphate dehydrogenase gene measured in (1) in each said test sample relative to the amount of the transcript of the glyceraldehyde-3-phosphate dehydrogenase gene measured in (1) a standard test sample that is to be used as a standard,
   (4) a fourth step of normalizing the amounts of the transcript of the desired gene measured in (2) in the test samples by multiplying the amount of the transcript of the desired gene measured in (2) in each test sample with the inverse of the ratio calculated in (3) for said test sample, and
   (5) comparing the normalized amounts of the transcript of the desired gene in two or more kinds of test samples, thereby measuring a difference in the relative amounts of the transcript of the desired gene in the test samples.

7. The method according to claim 6, wherein said test samples are samples derived from common marmoset.

8. The method according to claim 6, wherein the method of measuring an amount of a transcript of a gene in (1) and/or (2) is performed by either a DNA array method or a quantitative reverse transcriptase-polymerase chain reaction method.

9. A method for measuring a difference in levels of expression of a desired gene in two or more kinds of test samples by measuring a difference in amounts of a transcript of the desired gene in said samples, which comprises:
   (1) measuring an amount of a transcript of a common marmoset-derived glyceraldehyde-3-phosphate dehydrogenase gene in two or more kinds of test samples using a polynucleotide of claim 1,
   (2) measuring an amount of a transcript of a desired gene in said test samples using a polynucleotide for detecting the desired gene,
   (3) normalizing the amount of the transcript of the desired gene measured in (2) in the test samples by calculating the ratio of the amount of the transcript of the desired gene measured in (2) in each test sample relative to the amount of the transcript of the glyceraldehyde-3-phosphate dehydrogenase gene measured in (1) said test sample, and
   (4) comparing the normalized amounts of the transcript of the desired gene in two or more kinds of test samples, thereby measuring a difference in the relative amounts of the transcript of the desired gene in the test samples.

10. The method according to claim 9, wherein said test samples are samples derived from common marmoset.

11. The method according to claim 9, wherein the method of measuring an amount of a transcript of a gene is (1) and/or (2) is performed by either a DNA array method or a quantitative reverse transcriptase-polymerase chain reaction method.

12. An isolated polynucleotide consisting of a nucleotide sequence selected from the group consisting of:
   (1) the nucleotide sequence of SEQ ID NO:4 or 10;
   (2) the nucleotide sequence represented by nucleotide numbers 622 to 1221 of the nucleotide sequence of SEQ ID NO: 1;
   (3) a nucleotide sequence selected from the group consisting of:
      a consecutive nucleotide sequence of 60 nucleotides in length, which begins at any nucleotide of nucleotide number 805 to 806, 853 to 858, or 906 to 943 of the nucleotide sequence of SEQ ID NO: 1, and terminates at any nucleotide of nucleotide number 864 to 865, 912 to 917, or 965 to 1002 of the nucleotide sequence of SEQ ID NO: 1, respectively;
      a consecutive nucleotide sequence of 50 nucleotides in length, which begins at any nucleotide of nucleotide number 613, 643, 807 to 847, 902 to 927, 1005, 1039, 1057 to 1058, 1070 to 1086, or 1140 to 1160 of the nucleotide sequence of SEQ ID NO: 1, and terminates at any nucleotide of nucleotide number 662, 692, 856 to 896, 951 to 976, 1054, 1088, 1106 to 1107, 1119 to 1135 or 1189 to 1209 of the nucleotide sequence of SEQ ID NO: 1, respectively;
      a consecutive nucleotide sequence of 35 nucleotides in length, which begins at any nucleotide of nucleotide number 816 to 862, 902 to 942, 967 to 980, 1018, 1028 to 1042, 1070 to 1101, or 1150 to 1175 of the nucleotide sequence of SEQ ID NO: 1, and terminates at any nucleotide of nucleotide number 850 to 896, 936 to 976, 1001 to 1014, 1052, 1062 to 1076, 1104 to 1135, or 1184 to 1209 of the nucleotide sequence of SEQ ID NO: 1, respectively;
      a consecutive nucleotide sequence of 30 nucleotides in length, which begins at any nucleotide of nucleotide number 823 to 867, 902 to 945, 971 to 985, 1021 to 1037, 1070 to 1106, or 1152 to 1180 of the nucleotide sequence of SEQ ID NO: 1, and terminates at any nucleotide of nucleotide number 852 to 896, 931 to 974, 1000 to 1014, 1050 to 1066, 1099 to 1135, or 1181 to 1209 of the nucleotide sequence of SEQ ID NO: 1, respectively; and
      a consecutive nucleotide sequence of 20 nucleotides in length, which begins at any nucleotide of nucleotide number 836, 837, 859, 907, 908, 910, 921, 993, 994, 1004, 1032 or 1082 of the nucleotide sequence of SEQ ID NO: 1, and terminates at any nucleotide of nucleotide number 855, 856, 878, 926, 927, 929, 940, 1012, 1013, 1023, 1051 or 1101 of the nucleotide sequence of SEQ ID NO: 1, respectively; and
   (4) a nucleotide sequence which is fully complementary to any of the nucleotide sequences as defined in (1) to (3).

13. A composition for detecting DNA or RNA, which comprises a polynucleotide of claim 12.

14. The composition according to claim 13, wherein said polynucleotide is immobilized on a carrier.

15. A method for measuring a difference in levels of expression of a desired gene in two or more kinds of test samples by measuring a difference in amounts of a transcript of the desired gene in said samples, which comprises:
   (1) measuring an amount of a transcript of a common marmoset-derived glyceraldehyde-3-phosphate dehydrogenase gene in two or more kinds of test samples using a polynucleotide of claim 12, (2) measuring an amount of a transcript of a desired gene in said test samples using a polynucleotide for detecting the desired gene, (3) normalizing the amount of the transcript of the desired gene measured in (2) in each test sample by using as an internal standard the amount of the transcript of the glyceraldehyde-3-phosphate dehydrogenase gene measured in (1) in said test sample, and (4) comparing the normalized amounts of the transcript of the desired gene in two or more kinds of test samples, thereby measuring a difference in the relative amounts of the transcript of the desired gene in the test sample.

16. The method according to claim 15, wherein said test samples are samples derived from common marmoset.

17. A method for measuring a difference in levels of expression of a desired gene in two or more kinds of test samples by measuring a difference in amounts of a transcript of the desired gene in said samples, which comprises:

(1) measuring an amount of a transcript of a common marmoset-derived glyceraldehyde-3-phosphate dehydrogenase gene in two or more kinds of test samples using a polynucleotide of claim 12, (2) measuring an amount of a transcript of a desired gene in said test samples using a polynucleotide for detecting the desired gene, (3) calculating an inverse of the ratio of the amount of the transcript of the glyceraldehyde-3-phosphate dehydrogenase gene measured in (1) in each said test sample relative to the amount of the transcript of the glyceraldehyde-3-phosphate dehydrogenase gene measured in (1) a standard test sample that is to be used as a standard, (4) normalizing the amounts of the transcript of the desired gene measured in (2) in the test samples by multiplying the amount of the transcript of the desired gene measured in (2) in each test sample with the inverse of the ratio calculated in (3) for said test sample, and (5) comparing the normalized amounts of the transcript of the desired gene in two or more kinds of test samples, thereby measuring a difference in the relative amounts of the transcript of the desired gene in test samples.

18. The method according to claim 17, wherein said test samples are samples derived from common marmoset.

19. The method according to claim 17, wherein the method of measuring an amount of a transcript of a gene in (1) and/or (2) is performed by either a DNA array method or a quantitative reverse transcriptase-polymerase chain reaction method.

20. A method for measuring a difference in levels of expression of a desired gene in two or more kinds of test samples by measuring a difference in amounts of a transcript of the desired gene in said samples, which comprises:

(1) measuring an amount of a transcript of a common marmoset-derived glyceraldehyde-3-phosphate dehydrogenase gene in two or more kinds of test samples using a polynucleotide of claim 12, (2) measuring an amount of a transcript of a desired gene in said test samples using a polynucleotide for detecting the desired gene, (3) normalizing the amount of the transcript of the desired gene measured in (2) in the test samples by calculating the ratio of the amount of the transcript of the desired gene measured in (2) in each test sample relative to the amount of the transcript of the glyceraldehyde-3-phosphate dehydrogenase gene measured in (1) in said test sample, and (4) comparing the normalized amounts of the transcript of the desired gene in two or more kinds of test samples, thereby measuring a difference in the relative amounts of the transcript of the desired gene in the test samples.

21. The method according to claim 20, wherein said test samples are samples derived from common marmoset.

22. The method according to claim 20, wherein the method of measuring an amount of a transcript of a gene in (1) and/or (2) is performed by either a DNA array method or a quantitive reverse transcriptase-polymerase chain reaction method.

* * * * *

SEQUENCE LISTING

```
<160> NUMBER OF SEQ ID NOS: 10

<210> SEQ ID NO 1
<211> LENGTH: 1221
<212> TYPE: DNA
<213> ORGANISM: Callithrix Jacchus
<220> FEATURE:
<221> NAME/KEY: CDS
<222> LOCATION: (1)..(1008)

<400> SEQUENCE: 1
```

-continued

```
atggggaagg tgaaggtcgg agtcaacgga tttggtcgta tcgggcgcct ggtcaccaga      60
gctgctttta actctggtaa agtggatgtc gtcgccatca atgatccctt catcgacctc     120
aactacatgg tctacatgtt ccagtatgat tccacccatg gcaaattcca tggcactgtc     180
aaggctgaga acgggaagct tgtcatcaat ggaaatccca tcaccatctt ccaggagcga     240
gatccctcca aaatcaagtg gggcgatgct ggcgctgagt atgtggtgga gtccactggc     300
gtcttcacca ccatggagaa ggctggggct cacttgcagg ggggagccaa aagggtcatc     360
atatctgccc cctctgctga tgcccccatg ttcgtgatgg gcgtgaacca tgagaagtat     420
gacaacagcc tcaagatcgt cagcaacgcc tcctgcacca ccaactgctt agcgcccctg     480
gccaaggtca tccatgacaa ctttggtatc gtggaaggac tcatgaccac cgtccatgcc     540
atcactgcca cccagaagac cgtggatggc ccctccggga actgtggcg tgatggccgt     600
ggggctctcc agaacatcat ccctgcctct actggcgctg ccaaggccgt gggcaaggtc     660
atccctgagc tgaacgggaa gctcactggc atggccttcc gtgtccccac tgccaacgtg     720
tcagtggtgg acctgacctg ccgcctggaa aaacctgcca aatatgatga catcaagaag     780
gtggtgaagc aggcgtcgga gggcccccctc aagggcatcc tgggctacac tgagcaccag     840
gtggtgtcct ctgacttcaa cagcgacacc cattcttcca ccttcgatgc tggggctggc     900
attgccctca cgaccactt cgtcaagctc atttcctggt atgacaatga atttggctac     960
agcaacaggg tggtggacct catgtcccac atggcctcca aggaataaga ccctggacc    1020
accagcccca gcgagagcac gagaggaaaa gaggccctca ctcctgggga gtccctgcca    1080
cactgagtcc ctcaccacac cgaattgccc ctcctcacag tttccatgca gaccccttga    1140
agaaggaggg gcctagggag ccccaccttg tcgtgtacca tcaataaagt ccctgtgct    1200
cagccaaaaa aaaaaaaaaa a                                              1221
```

<210> SEQ ID NO 2
<211> LENGTH: 335
<212> TYPE: PRT
<213> ORGANISM: Callithrix Jacchus

<400> SEQUENCE: 2

```
Met Gly Lys Val Lys Val Gly Val Asn Gly Phe Gly Arg Ile Gly Arg
  1               5                  10                  15

Leu Val Thr Arg Ala Ala Phe Asn Ser Gly Lys Val Asp Val Val Ala
             20                  25                  30

Ile Asn Asp Pro Phe Ile Asp Leu Asn Tyr Met Val Tyr Met Phe Gln
         35                  40                  45

Tyr Asp Ser Thr His Gly Lys Phe His Gly Thr Val Lys Ala Glu Asn
     50                  55                  60

Gly Lys Leu Val Ile Asn Gly Asn Pro Ile Thr Ile Phe Gln Glu Arg
 65                  70                  75                  80

Asp Pro Ser Lys Ile Lys Trp Gly Asp Ala Gly Ala Glu Tyr Val Val
                 85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Val Ser Asn Ala Ser Cys Thr Thr Asn Cys Leu Ala Pro Leu
```

```
                145                 150                 155                 160
Ala Lys Val Ile His Asp Asn Phe Gly Ile Val Glu Gly Leu Met Thr
                    165                 170                 175

Thr Val His Ala Ile Thr Ala Thr Gln Lys Thr Val Asp Gly Pro Ser
                180                 185                 190

Gly Lys Leu Trp Arg Asp Gly Arg Gly Ala Leu Gln Asn Ile Ile Pro
            195                 200                 205

Ala Ser Thr Gly Ala Ala Lys Ala Val Gly Lys Val Ile Pro Glu Leu
        210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
                260                 265                 270

Ile Leu Gly Tyr Thr Glu His Gln Val Val Ser Ser Asp Phe Asn Ser
            275                 280                 285

Asp Thr His Ser Ser Thr Phe Asp Ala Gly Ala Gly Ile Ala Leu Asn
        290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ser His Met Ala Ser Lys Glu
                325                 330                 335

<210> SEQ ID NO 3
<211> LENGTH: 20
<212> TYPE: DNA
<213> ORGANISM: Artificial sequence
<220> FEATURE:
<223> OTHER INFORMATION: Designed oligonucleotide primer for PCR

<400> SEQUENCE: 3
atggggaagg tgaaggtcgg                                                      20

<210> SEQ ID NO 4
<211> LENGTH: 20
<212> TYPE: DNA
<213> ORGANISM: Artificial sequence
<220> FEATURE:
<223> OTHER INFORMATION: Designed oligonucleotide primer for PCR

<400> SEQUENCE: 4
ttattccttg gaggccatgt                                                      20

<210> SEQ ID NO 5
<211> LENGTH: 35
<212> TYPE: DNA
<213> ORGANISM: Artificial sequence
<220> FEATURE:
<223> OTHER INFORMATION: Designed oligonucleotide primer for PCR

<400> SEQUENCE: 5
gactcgagtc gacatcgatt tttttttttt ttttt                                     35

<210> SEQ ID NO 6
<211> LENGTH: 18
<212> TYPE: DNA
<213> ORGANISM: Artificial sequence
<220> FEATURE:
<223> OTHER INFORMATION: Designed oligonucleotide primer for PCR
```

-continued

```
<400> SEQUENCE: 6
gactcgagtc gacatcga                                                    18

<210> SEQ ID NO 7
<211> LENGTH: 19
<212> TYPE: DNA
<213> ORGANISM: Artificial sequence
<220> FEATURE:
<223> OTHER INFORMATION: Designed oligonucleotide primer for
      determination of DNA nucleotide sequence

<400> SEQUENCE: 7
tatttaggtg acactatag                                                   19

<210> SEQ ID NO 8
<211> LENGTH: 20
<212> TYPE: DNA
<213> ORGANISM: Artificial sequence
<220> FEATURE:
<223> OTHER INFORMATION: Designed oligonucleotide primer for
      determination of DNA nucleotide sequence

<400> SEQUENCE: 8
taatacgact cactataggg                                                  20

<210> SEQ ID NO 9
<211> LENGTH: 18
<212> TYPE: DNA
<213> ORGANISM: Artificial sequence
<220> FEATURE:
<223> OTHER INFORMATION: Designed oligonucleotide primer for RT-PCR

<400> SEQUENCE: 9
aagggcatcc tgggctac                                                    18

<210> SEQ ID NO 10
<211> LENGTH: 18
<212> TYPE: DNA
<213> ORGANISM: Artificial sequence
<220> FEATURE:
<223> OTHER INFORMATION: Designed oligonucleotide primer for RT-PCR

<400> SEQUENCE: 10
gggcctcttt tcctctcg                                                    18
```